United States Patent Office

Re. 28,225
Reissued Nov. 5, 1974

28,225

PHOTOBLEACHABLE DYE COMPOSITIONS

Donald W. Heseltine, Philip W. Jenkins and John D. Mee, Rochester, N.Y., assignors to Eastman Kodak Company, Rochester, N.Y.

No Drawing. Original No. 3,615,432, dated Oct. 26, 1971, Ser. No. 766,307, Oct. 9, 1968. Application for reissue Apr. 30, 1973, Ser. No. 356,674
Int. Cl. G03c *1/72, 5/04*
U.S. Cl. 96—27 R 34 Claims

Matter enclosed in heavy brackets [ ] appears in the original patent but forms no part of this reissue specification; matter printed in italics indicates the additions made by reissue.

ABSTRACT OF THE DISCLOSURE

A class of energy-sensitive compounds containing heterocyclic nitrogen atoms substituted with an —OR group fragment under the influence of various forms of energy to form a dye base, a proton and an aldehyde, these materials being useful in image reproduction.

This invention relates to a novel class of organic compounds and to novel photographic elements, compositions and processes using these compounds.

Various classes of dyes have known uses in different types of photographic systems. Perhaps one of the most common applications of dyes is their use as spectral sensitizers in silver halide emulsions. The native sensitivity of most silver halide emulsions falls within a very limited range of the visible portion of the spectrum (generally the blue region only'. However, it is known that when certain dyes are added to silver halide emulsions, the sensitivity of the silver halide emulsion is extended to longer wavelengths. The sensitizing dyes are incorporated in the emulsion and are generally uniformly distributed throughout the emulsion. The methods used to incorporate the dyes are well known to those skilled in the art.

Dyes are also used to sensitize silver halide emulsions which produce direct positive images. Emulsions of this type may contain an electron acceptor and silver halide grains that have been fogged with a combination of a reducing agent and a compound of a metal more electropositive than silver. One of the advantages of such direct positive emulsions is that the highlight areas of the images obtained with these materials are substantially free from fog. However, known materials of this type have not exhibited the high speed required for many applications of photography. Also, such known materials have not shown the desired selective sensitivity, especially to radiation in the green to red region of the spectrum. Furthermore, in some instances as with known indole cyanine dyes, the inclusion of color-forming couplers or colored couplers in such emulsions has tended to reduce the sensitivity thereof in proportion to the length of the holding time, i.e., the time period from actual making the coating and curing the emulsion. This is a decided disadvantage since such emulsions cannot be held for any substantial period of time but must be coated immediately as formulated. It is apparent, therefore, that there is need in the art for improved direct positive photographic emulsions having not only good speed and selective sensitivity, but having, in addition, desirable holding or keeping stability.

In nonsilver photographic systems, bleachable dyes can be used as photosensitive materials. Generally, these dyes are bleached in proportion to the exposure and direct positive images are attainable. Color direct positives are produced by an appropriate mixture of photobleachable cyan, magenta and yellow dyes. The loss of color usually proceeds at a relatively slow rate and even the use of sensitizers does not speed up the process enough to make it commercially attractive.

Dyes are also useful in thermographic systems. Recording elements frequently are impregnated with dyes which change color when subjected to localiped heating. The heat necessary to cause the dye to react can be provided either by direct contact, such as hot stylus, or by exposure of a differentially radiation-absorptive graphic original to intense radiant energy while in contact with a dye-containing heat-sensitive element. The heat pattern established at the irradiated original causes a corresponding visible pattern to appear in the heat-sensitive layer, without deterioration of the original. A convenient source of radiation for thermographic reproduction is a tungsten filament lamp. The radiation is rich in infrared as well as visible light, and the process is particularly suited to the copying of originals having infrared-absorptive image areas. Certain of these thermographic materials which have been previously described are only slightly sensitive to visible light, and consequently, prolonged exposures are necessary in order to produce acceptable copies. It is obvious that such materials have only limited use, and, in certain instances, cannot be used at all on a commercial basis.

Still another use of dyes in sensitive photographic elements is in layers for the reduction of halation or filtration of certain undesirable rays from the exposing radiation, either upon direct exposure or for reexposure in a photographic reversal process. Antihalation layers can be coated as backing layers on either side of a transparent support carrying the light-sensitive composition. Light-filtering layers can be coated over the light-sensitive layers or between such layers in multilayer elements. The dyes used for such layers must have the desired spectral absorption characteristics. They should be easily incorporated in a water-permeable hydrophilic colloidal layer and yet firmly held in the layer so that they do not diffuse from it either during the manufacture of the element or on storing it. It is generally necessary to employ light-filtering dyes which can be quickly and readily rendered ineffective, i.e., decolorized or destroyed and removed prior to, during, or after photographic processing. For many purposes it is particularly convenient to employ dyes which are rendered ineffective by one of the photographic baths used in processing the exposed element, such as photographic developer or fixer in the case of silver halide photography. Prior art dyes which have desirable absorption characteristics have not always had good bleaching characteristics and reproductions made from photographic elements containing them have been subject to undesirable stains. Other dyes have not had the stability in aqueous gelatin that is desired.

It is an object of this invention to provide a novel class of energy-sensitive compounds.

Another object of this invention is to provide novel image-forming compositions and elements containing these compounds.

It is still another object of this invention to provide negative photographic silver halide emulsions sensitized with these novel compounds.

Another object is to provide novel photographic elements containing negative silver halide emulsions sensitized with these compounds.

It is another object of this invention to provide direct positive silver halide emulsions containing these novel compounds.

It is also an object to provide novel photographic elements having direct positive silver halide emulsions containing these compounds.

Another object is to provide novel direct positive silver halide emulsions containing these compounds and a color former.

An object of this invention is also to provide heat-sensitive elements containing these novel compounds.

Another object is to provide novel dye-containing photobleachable elements.

Another object is to provide novel nonsilver direct positive dye-bleach photographic elements capable of producing full color photographic prints.

It is still a further object of this invention to provide photographic elements having novel bleachable filter layers.

Also, an object is to provide photographic elements having novel antihalation layers.

It is another object of this invention to provide novel processes for producing images using novel compositions, compounds and elements.

These and other objects of the invention are accomplished with compounds having one of the general formulas:

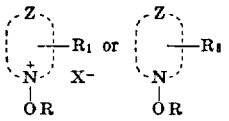

wherein:

$R_1$ can be any of the following:

a. a methine linkage terminated by a heterocyclic nucleus of the type contained in cyanine dyes, e.g., those set forth in Mees and James, "The Theory of the Photographic Process," MacMillan, third ed., pp. 198–232; the methine linkage can be substituted or unsubstituted, e.g., $$—CH=,\ —C(CH_3)=,\ —C(C_6H_5)=,\ —CH=CH—,\ —CH=CH—CH=,\ \text{etc.};$$

b. an alkyl radical preferably containing 1 to 8 carbon atoms including a substituted alkyl radical;

c. an aryl radical including a substituted aryl radical such as a phenyl radical, a naphthyl radical, a tolyl radical, etc.;

d. a hydrogen atom;

e. an acyl radical having the formula $$—\overset{O}{\overset{\|}{C}}—R$$

wherein R is hydrogen or an alkyl group preferably having 1 to 8 carbon atoms;

f. an anilinovinyl radical such as a radical having the formula

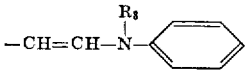

wherein $R_3$ is hydrogen or alkyl; or g. a styryl radical including substituted styryl radicals, e.g.,

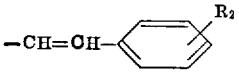

wherein $R_2$ is hydrogen, alkyl, aryl, amino including dialkylamino such as dimethylamino;

$R_8$ can be either of the following:

a. a methine linkage terminated by a heterocyclic nucleus of the type contained in merocyanine dyes, e.g., those set forth in Mees and James (cited above); the methine linkage can be substituted or unsubstituted; or b. an allylidene radical including a substituted allylidene radical such as a cyanoallylidene radical, an alkylcarboxyallylidene radical or an alkylsulfonylallylidene radical;

R can be either:

a. an alkyl radical preferably having 1 to 8 carbon atoms such as methyl, propyl, ethyl, butyl, etc., including a substituted alkyl radical such as sulfoalkyl, e.g., $$—(CH_2)_3SO_3—,$$

an aralkyl, e.g., benzyl or pyridinato-oxyaklyl salt,, e.g., $—(CH_2)_3—O—Y$ wherein Y is a substituted or unsubstituted pyridinium salt;

b. an acyl radical, e.g., $$—\overset{O}{\overset{\|}{C}}—R_4$$

wherein $R_4$ is an alkyl radical preferably having 1 to 8 carbon atoms or aryl radical, e.g., methyl, ethyl, propyl, butyl, phenyl, naphthyl, etc.;

c. an aryl radical including a substituted aryl radical, e.g., phenyl, naphthyl, tolyl, etc., Z represents the atoms necessary to complete a 5 to 6 membered heterocyclic nucleus including a substituted heterocyclic nucleus which nucleus can contain at least one additional hetero atom such as oxygen, sulfur, selenium or nitrogen, e.g., a pyridine nucleus, an indole nucleus, a quinoline nucleus, etc.; and X represents an acid anion, e.g., chloride, bromide, iodide, perchlorate, sulfamate, thiocyanate, p-toluenesulfonate, methyl sulfate, tetrafluoroborate, etc.

These compounds are very versatile and can function in several different manners when used in photographic elements. They can be used as sensitizers in both direct positive and negative silver halide emulsions; they are heat bleachable and thus useful in thermographic recording elements; they are photobleachable and can be used for producing direct positives merely by coating them on a substrate; they make excellent antihalation layers and filter layers since they can be removed without the use of special baths simply by subjecting them to light for a sufficient period of time; and, when a mixture of a cyan, a magenta and a yellow dye having the above formula are coated on a support and exposed to a colored transparency, a direct color positive is obtained as a result of photobleaching. They are also useful in preparing holographic elements.

The compounds of this invention are chemically altered when subjected to various forms of energy such as (1) electromagnetic radiation including ultraviolet, visible and infrared light, X-rays, electron beams, laser beams, etc., (2) heat derived from various sources such as infrared radiation, (3) energy produced by mechanical means such as that produced by the local application of pressure, (4) sound waves, etc.

When the energy sensitive compounds of this invention are exposed to any of the various forms of energy enumerated above, the pursuant alteration is generally a fragmentation of the compound molecule. It is the resultant components of the fragmentation which may be used in the formation of images. The particular route of the fragmentation reaction is somewhat dependent upon the structure of the original compound. However, based upon observations, it is believed that the route followed when a dye of this invention (such as the one given below is exposed to a form of energy (such as light) is the following:

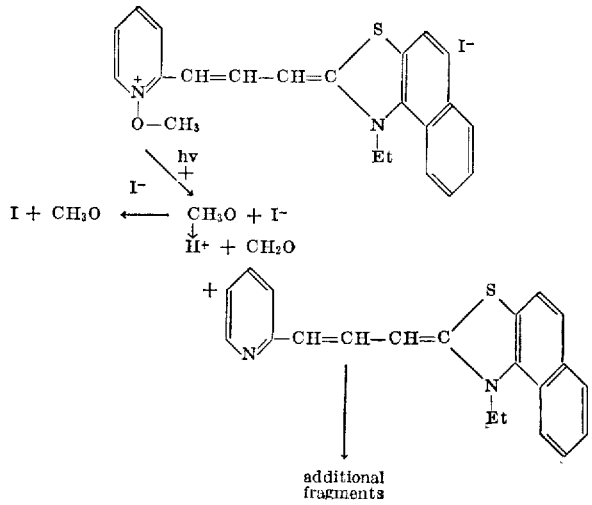

In this case photobleaching is effected by a heterolytic cleavage of the nitrogen-oxygen (N–O) bond to produce a $RO^+$ ion and a dye base which may in part fragment even farther. The dye base is useful in image reproduction. The remaining fragments are useful as initators for other reactions such as polymerization and cross-linking as described in our copending application Ser. No. 766,304 titled "Photopolymerization" and our copending application Ser. No. 766,280 titled "Crosslinkable Polymer Compositions" filed concurrently herewith [.] , *now U.S. Pat. Nos. 3,574,622 (issued Apr. 13,1971) and 3,615,453 (issued Oct. 26,1971), respectively*. The original color of the dye appears when it is treated with acid so that the pH of the material is below 7, but no further photobleaching results when the dye is exposed to energy. Each of the fragments produced can be used in various processes, e.g., the aldehyde is an effective cross-linking agent as described in the aforementioned application, or as a dye mordant. The free radicals and cations are useful as polymerization initiators as described in the aforementioned application.

While certain compounds of this invention are more effective for a particular utility than others, the preferred ones have one of the following structures:

(A)

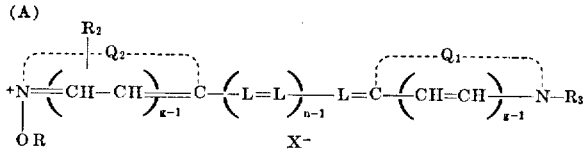

(B)

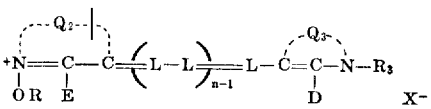

(C)

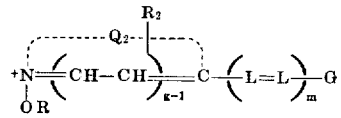

(D)

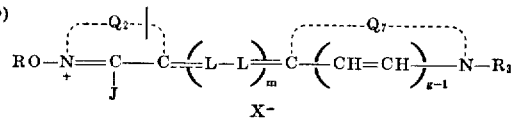

(E)

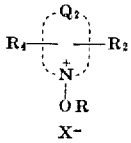

(F)

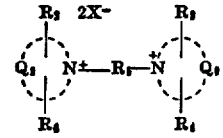

(G)

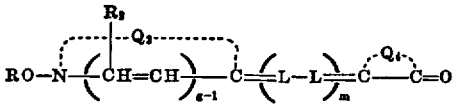

(H)

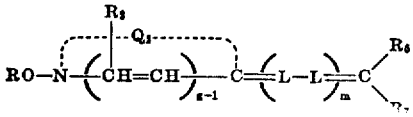

wherein $Q_1$, $Q_2$, $Q_3$, $Q_7$ and $Q_9$ each represent the nonmetallic atoms necessary to complete a sensitizing or desensitizing nucleus containing 5 or 6 atoms in the heterocyclic ring, which nucleus can contain at least one additional hetero atom such as oxygen, sulfur, selenium or nitrogen, i.e., a nucleus of the type used in the production of cyanine dyes, such as the following representative nuclei: a thiazole nucleus, e.g., thiazole, 4-methylthiazole, 3-ethylthiazole, 4-phenylthiazole, 5-methylthiazole, 5-phenylthiazole, 4,5-dimethylthiazole, 4,5-diphenylthiazole, 4-(2-thienyl)thiazole, benzothiazole, 4-chlorobenzothiazole, 4- or 5-nitrobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 6-nitrobenzothiazole, 5-bromobenzothiazole, 6-bromobenzothiazole, 5-chloro-6-nitrobenzothiazole, 4-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, a tetrahydrobenzothiazole nucleus, 5,6-dimethoxybenzothiazole, 5,6-methylenedioxybenzothiazole, 5-hydroxybenzothiazole, 6-hydroxybenzothiazole, α-naphthothiazole, β-naphthothiazole, ββ-naphthothiazole, 5-methoxy-ββ-naphthothiazole, 5-ethoxy-β-naphthothiazole, 8-methoxy - α - naphthothiazole, 7-methoxy-α-naphthothiazole, 4′ - methoxythianaphtheno-7′,6′,4,5-thiazole, nitro group substituted naphthothiazoles, etc.; an oxazole nucleus, e.g., 4-methyloxazole, 4-nitro-oxazole, 5-methyloxazole, 4-phenyloxazole, 4,5-diphenyloxazole, 4-ethyloxazole, 4,5-dimethyloxazole, 5-phenyloxazole, benzoxazole, 5-chlorobenzoxazole, 5-methylbenzoxazole, 5-phenylbenzoxazole, 5- or 6-nitrobenzoxazole, 5-chloro-6-nitrobenzoxazole, 6 - methylbenzoxazole, 5,6 - dimethylbenzoxazole, 4,6 - dimethylbenzoxazole, 5-methoxybenzoxazole, 5 - ethoxybenzoxazole, 5 - chlorobenzoxazole, 6-methoxybenzoxazole, 5 - hydroxybenzoxazole, 6 - hydroxybenzoxazole, α - naphthoxazole, β - naphthoxazole, nitro group substituted naphthoxazole, etc.; a selenazole nucleus, e.g., 4-methylselenazole, 4-nitroselenazole, 4-phenylselenazole, benzoselenazole, 5-chlorobenzoselenazole, 5-methoxybenzoselenazole, 5-hydroxybenzoselenazole, 5- or 6 - nitrobenzoselenazole, 5-chloro-6-nitrobenzoselenazole, tetrahydrobenzoselenazole, α-naphthoselenazole, β-naphthoselenazole, nitro group substituted naphthoselenazoles, etc.; a thiazoline nucleus, e.g., thiazoline, 4-methylthiazoline, etc.; a pyridine nucleus, e.g., 2-nyridine, 5-methyl-2-pyridine, 4-pyridine, 3-methyl-4-pyridine, nitro group substituted pyridines, etc., a quinoline nucleus, e.g., 2-quinoline, 3 - methyl - 2 - quinoline, 5 - ethyl - 2 - quinoline, 6 - chloro - 2 - quinoline, 6 - nitro - 2 - quinoline, 8-chloro - 2 - quinoline, 6 - methoxy - 2 - quinoline, 8-ethoxy - 2 - quinoline, 8 - hydroxy - 2 - quinoline, 4-quinoline, 6-methoxy - 4 - quinoline, 6-nitro-4-quinoline, 7-methyl-4-quinoline, 8-chloro-4-quinoline, 1-isoquinoline, 6-nitro-1-isoquinoline, 3,4-dihydro-1-isoquinoline, 3-isoquinoline, etc.; a 3,3-dialkylindolenine nucleus, preferably having a nitro or cyano substituent, e.g., 3,3-dimethyl-5 or 6-nitroindolenine, 3,3-dimethyl-5- or 6-cyanoindolenine, etc.; and, an imidazole nucleous, e.g., imidazole, 1-alkylimidazole, 1-alkyl-4-phenylimidazole, 1-alkyl-4,5-dimethylimidazole, benzimidazole, 1-alkylbenzimidazole, 1-alkyl-5-nitrobenzimidazole, 1 - aryl-5,6-dichlorobenzimidazole, 1-alkyl-α-naphthimidazole, 1-aryl-β-naphthimidazole; 1-alkyl - 5 - methoxy-α-naphthimidazole, or, an imidazo [4,5-b]quinoxaline nucleus, e.g., 1-alkylimidazo-[4,5-b]quinoxaline such as 1-ethylimidazo[4,5-b]quinoxaline, 6 - chloro - 1 - ethylimidazo[4,5-b]quinoxaline, etc., 1-alkenylimidazo[4,5-b]quinozaline, such as 1-allylimidazo[4,5-b]quinoxaline 6 - chloro - 1 - allylimidazo[4,5-b] quinoxaline, etc., 1-arylimidazo[4,5-b]quinoxaline such as 1-phenylimidazo[4,5-b]quinoxaline, 6 - chloro-1-phenylimidazo[4,5-b]quinoxaline, etc.; a 3,3-dialkyl-3H-pyrrolo-[2,3-b]pyridine nucleus, e.g., 3,3 - dimethyl - 3H - pyrrolo-[2,3-b]pyridine, 3,3 - diethyl - 3H - pyrrolo[2,3-b]pyridine, etc.; a thiazolo[4,5-b]quinoline nucleus; an indolyl nucleus including substituted indolyl nuclei such as a 2-phenyl-3-indole, 1 - methyl - 2 - phenyl-3-indole; and the like; $R_3$ represents an alkyl group, including substituted alkyl (preferably a lower alkyl containing from 1 to 4 carbon atoms), e.g., methyl, ethyl, propyl, isopropyl, butyl, hexyl, cyclohexyl, decyl, dodecyl, etc., and substituted alkyl groups (preferably a substituted lower alkyl containing from 1 to 4 carbon atoms), such as a hydroxy-alkyl group. e.g., β-hydroxyethyl, ω-hydroxybutyl, etc., an alkoxyalkyl group, e.g., β-methoxyethyl, ω-butoxybutyl, etc., a carboxyalkyl group, e.g., β-carboxyethyl, ω-carboxybutyl, etc., an alkoxy group, e.g., methoxy, ethoxy, etc., a sulfoalkyl group, e.g., β-sulfoethyl, ω-sulfobutyl, etc., a sulfatoalkyl group, e.g., β-sulfatoethyl, ω-sulfatobutyl, etc., an acyloxyalkyl group, e.g., β-acetoxyethyl, ω-acetoxypropyl, ω-butyryloxybutyl, etc., an alkoxycarbonylalkyl group, e.g., β-methoxycarbonylethyl, ω-ethoxycarbonylbutyl, etc. or an aralkyl group, e.g., benzyl, phenethyl, etc.; an alkenyl group, e.g., allyl, 1 - propenyl, 2-butenyl, etc., or an aryl group, e.g., phenyl, tolyl, naphthyl, methoxyphenyl, chlorophenyl, etc.; $Q_4$ represents the nonmetallic atoms required to complete a 5 to 6 membered heterocyclic nucleus, typically containing a hetero atom selected from nitrogen, sulfur, selenium, and oxygen, such as a 2-pyrazolin-5-one nucleus (e.g., 3-methyl - 1 - phenyl - 2 - pyrazolin - 5 - one, 1-phenyl-2-pyrazolin-5-one, 1 - (2 - benzothiazolyl) - 3 - methyl-2-pyrazolin - 5 - one, etc.); an isoxazolone nucleus (e.g., 3-phenyl-5-(4H)-isoxazoline, 3 - methyl - 5 - (4H) - isoxazolone, 3 - methyl - 5 - (4H) - isoxazolone, etc.); an oxindole nucleus (e.g., 1-alkyl - 2,3 - dihydro - 2 - oxindoles, etc.), a 2,4,6-triketohexahydropyrimidine nucleus (e.g., barbituric acid or 2-thiobarbituric acid as well as their 1-alkyl (e.g., 1-methyl, 1-ethyl, 1-propyl, 1-heptyl, etc.) or 1,3-dialkyl (e.g., 1,3-dimethyl, 1,3-diethyl, 1,3-dipropyl, 1,3 - diisopropyl, 1,3 - dicyclohexyl, 1,3 - di(β-methoxyethyl), etc.) or 1,3-diaryl (e.g., 1,3-diphenyl, 1,3-di(p-chlorophenyl), 1,3-di(p-ethoxycarbonylphenyl), etc.) or 1-aryl (e.g., 1-phenyl, 1-p-chlorophenyl, 1-p-ethoxycarbonylphenyl), etc.) or 1-alkyl - 3 - aryl (e.g., 1-ethyl-3-phenyl, 1 - n - heptyl - 3 - phenyl, etc.) derivatives), a rhodanine nucleus (i.e., 2 - thio - 2,4 - thiazolidinedione series), such as rhodanine, 3-alkylrhodanines (e.g., 3-ethylrhodanine, 3-allylrhodanine, etc.), 3-carboxyalkylrhodanines (e.g., 3-(2-carboxyethyl)rhodanine, 3-(4-carboxybutyl)rhodanine, etc.), 3 - sulfoalkyl rhodanines (e.g., 3-(2-sulfoethyl)rhodanine, 3 - (3 - sulfopropyl)rhodanine, 3-(4-sulfobutyl)rhodanine, etc.), or 3-arylrhodanines (e.g., 3-phenylrhodanine, etc.), etc.; a 2(3H)-imidazo-[1,2-a]-pyridone nucleus; a 2-furanone nucleus (e.g., 3-cyano-4-phenyl-2(5H)-furanone); a thiophen - 3 - one-1,1-dioxide nucleus (e.g., benzo[b]thiophen-3(2H)-one-1,1-dioxide); a 5,7 - dioxo - 6,7 - dihydro-5-thiazolo[3,2-a]-pyrimidine nucleus (e.g., 5,7-dioxo-3-phenyl-6,7-dihydro-5-thiazolo[3,2-a]pyrimidine, etc.); a 2-thio-2,4-oxazolidinedione nucleus (i.e., those of the 2-thio-2,4-(3H,5H)-oxazoledione series) (e.g., 3-ethyl-2-thio-2,4-oxazolidinedione, 3-(2-sulfoethyl)-2-thio-2,4-oxazolidinedione, 3-(4-sulfobutyl) - 2 - thio - 2,4 - oxazolidinedione, 3-(3-carboxypropyl) - 2 - thio - 2,4 - oxazolidinedione, etc.); a thianaphthenone nucleus (e.g., 2-(2H)-thianaphthenone, etc.); a 2 - thio - 2,5 - thiazolidinedione nucleus (i.e., the 2 - thio - 2,5(3H,4H) - thiazoledione series) (e.g., 3-ethyl-2 - thio - 2,5 - thiazolidinedione, etc.); a 2,4 - thiazolidinedione nucleus (e.g., 2,4-thiazolidinedione, 3 - ethyl - 2,4-thiazolidinedione, 3 - phenyl - 2,4 - thiazolidinedione, 3-α-naphthyl - 2,4 - thiazolidinedione, etc.); a thiazolidinone nucleus (e.g., 4-thiazolidinone, 3-ethyl-4-thiazolidinone, 3-phenyl - 4 - thiazolidinone, 3 - α - naphthyl-4-thiazolidinone, etc.); a 2 - thiazolin - 4 - one series (e.g., 2 - ethylmercapto - 2 - thiazolin - 4 - one, 2-alkylphenylamino-2-thiazolin - 4 - one, 2 - diphenylamino-2-thiazolin-4-one, etc.); a 2-imino-4-oxazolidinone (i.e., pseudohydantoin) nucleus; a 2,4 - imidazolidinedione (hydantoin) series (e.g., 2,4 - imidazolidinedione, 3 - ethyl-2,4 - imidazolidinedione, 3 - phenyl - 2,4 - imidazolidinedione, 3-α-naphthyl - 2,4 - imidazolidinedione, 1,3-diethyl-2,4-imidazolinedione, 1 - ethyl - 3 - phenyl-2,4-imidazolidinedione, 1 - ethyl - 2 - α - naphthyl-2,4-imidazolidinedione, 1,3-diphenyl - 2,4 - imidazolidinedione, etc.); a 2 - thio - 2,4-imidazolidinedione (i.e., 2-thiohydantoin) nucleus (e.g., 2-thio-2,4-imidazolidinedione, 3-ethyl-2-thio - 2,4 - imidazolidinedione, 3 - (4 - sulfobutyl) - 2 - thio - 2,4 - imidazolidinedione, 3 - (2 - carboxyethyl) - 2 - thio-2,4-imidazolidinedione, 3 - phenyl - 2 - thio-2,4-imidazolidinedione, 3 - α - naphthyl - 2 - thio-2,4-imidazolidinedione, 1,3-diethyl - 2 - thio - 2,4 - imidazolidinedione, 1 - ethyl-3-phenyl-2-thio - 2,4 - imidazolidinedione, 1 - ethyl - 3 - naphthyl-2 - thio - 2,4 - imidazolidinedione, 1,3 - diphenyl - 2 -thio-2,4 - imidazolindinedione, etc.); a 2 - amidazolin-5-one nucleus (e.g., 2-proplymercapto - 2 - imidazolin-5-one. etc.);

n is a positive integer from 1 to 4;

m is a positive integer from 1 to 3;

g is a positive integer from 1 to 2;

$R_6$ and $R_7$ each represent a cyano radical, an ester radical such as ethoxycarbonyl, methoxycarbonyl, etc., or an alkylsulfonyl radical such as ethylsulfonyl, methylsulfonyl, etc.;

L represents a methine linkage having the formula $$-\underset{\underset{T}{|}}{C}=$$

wherein T is hydrogen, lower alkyl of one to four carbon atoms or aryl such as phenyl, e.g., —CH=, —C(CH₃)=, —C(C₆H₅)=, etc.;

D, E, J, $R_2$ and $R_4$ each represent a hydrogen atom, an alkyl group (preferably a lower alkyl containing from one to four carbon atoms), e.g., methyl, ethyl, propyl, isopropyl, butyl, decyl, dodecyl, etc., or an aryl group, e.g., phenyl, tolyl, naphthyl, methoxyphenyl, chlorophenyl, nitrophenyl, etc.;

X represents an acid anion, e.g., chloride, bromide, iodide, perchlorate, tetrafluoroborate, sulfamate, thiocyanate, p-toluenesulfonate, methyl sulfate, etc.;

G represents an anilino radical or an aryl radical, e.g., phenyl, naphthyl, dialkylaminophenyl, tolyl chlorophenyl, nitrophenyl, anilinovinyl, etc.;

$R_5$ is an alkyleneoxy radical havng one to eight carbon atoms in the alkylene chain including an alkylenedioxy radical and an arylenebisalkoxy radical, e.g., ethyleneoxy, trimethyleneoxy, tetramethyleneoxy, propylideneoxy, ethylenedioxy, phenylenebisethoxy, etc.;

R represents either (1) an alkyl radical including a substituted alkyl (preferably a lower alkyl having one to four carbon atoms), e.g., methyl, ethyl, propyl, isopropyl, butyl, hexyl, cyclohexyl, decyl, dodecyl, aralkyl such as benzyl, sulfoalkyl such as β-sulfoethyl, ω-sulfobutyl, ω-sulfopropyl; or (2) an acyl radical e.g., $$-\overset{\overset{O}{\|}}{C}-R_8$$

wherein $R_8$ is an alkyl including a substituted alkyl or an aryl radical such as methyl, phenyl, naphthyl, propyl, benzyl, etc.

In the above formulas $Q_2$ preferably completes a pyridine, an indole or a quinoline nucleus. Also, D, E, and J are preferably aryl radicals. Nuclei wherein $Q_1$, $Q_2$, $Q_3$, $Q_7$ and $Q_9$ complete an imidazo [4,5-b]quinoxaline nucleus, or a nitro group thiazole, oxazole, selenazole, thiazoline, pyridine, quinoline, indole, or imidazole nucleus are referred to hereafter as desensitizing nuclei.

Typical compounds and intermediates included in the scope of this invention are the following:

1. 3-ethyl-1'-methoxyoxa-2'-pyridocarbocyanine perchlorate
2. 1'-ethoxy-3-ethyloxa-2'-pyridocarbocyanine tetrafluoroborate
3. 3'-ethyl-1-methoxy-2-pyridothiacyanine iodide
4. 1-ethoxy-3'-ethyl-2-pyridothiacyanine tetrafluoroborate
5. 1-benzyloxy-3'-ethyl-2-pyridothiacyanine iodide
6. 3'-ethyl-1-methoxy-2-pyridothiacarbocyanine iodide
7. 1-ethoxy-3'-ethyl-2-pyridothiacarbocyanine tetrafluoroborate
8. anhydro-3'-ethyl-1-(3-sulfopropoxy)-2-pyridothiacarbocyanine hydroxide 9. 1-benzyloxy-3'-ethyl-2'-pyridothiacarbocyanine perchlorate
10. 3'-ethyl-1-methoxy-2-pyridothiacarbocyanine perchlorate
11. 1'-methoxy-1,3,3-trimethylindo-2'-pyridocarbocyanine picrate
12. 3'-ethyl-1-methoxy-4',5'-benzo-2-pyridothiacarbocyanine perchlorate
13. 1-ethoxy-3'-ethyl-4',5'-benzo-2-pyridothiacarbocyanine tetrafluoroborate
14. 1'-ethoxy-3-ethyloxa-2'-carbocyanine tetrafluoroborate
15. 1'-ethoxy-3-ethylthia-2'-cyanine tetrafluoroborate
16. 1'-ethoxy-3-ethylthia-2'-carbocyanine tetrafluoroborate
17. 1'-ethoxy-3-ethylthia-2'-dicarbocyanine tetrafluoroborate
18. 1-methoxy-3'-methyl-2-pyridothiazolinocarbocyanine perchlorate
19. 3'-ethyl-1-methoxy-4-pyridothiacyanine perchlorate
20. 3'-ethyl-1-methoxy-4-pyridothiacarbocyanine perchlorate
21. 1,1'-dimethoxy-2,2'-diphenyl-3,3'-indolocarbocyanine perchlorate
22. 1-methoxy-1'-methyl-2,2',10-triphenyl-3,3'-indolocarbocyanine perchlorate
23. 1,1'-diethoxy-2,2'-diphenyl-3,3'-indolocarbocyanine perchlorate
24. 1-ethoxy-1'-methyl-2,2',10-triphenyl-3,3'-indolocarbocyanine perchlorate
25. 1'-ethoxy-3-ethyl-4,5-benzothia-2'-carbocyanine tetrafluoroborate
26. 2-β-anilinovinyl-1-methoxypyridinium p-toluenesulfonate
27. 1-ethyl-1'-methoxy-4,5-benzothia-4'-carbocyanine perchlorate
28. 3'-ethyl-1-methoxy-6'-nitro-2-phenyl-3-indolothiacarbocyanine p-toluenesulfonate
29. 1-ethoxy-3'-ethyl-6'-nitro-2-phenyl-3-indolothiacarbocyanine p-toluenesulfonate
30. 1,3-diallyl-1'-methoxy-2'-phenylimidazo[4,5-b]quinoxalino-3'-indolocarbocyanine perchlorate
31. 1,3-diallyl-1'-ethoxy-2'-phenylimidazo[4,5-b]quinoxalino-3'-indolocarbocyanine perchlorate
32. 1-methoxy-2-methylpyridinium p-toluenesulfonate
33. 1-methoxy-4-methylpyridinium p-toluenesulfonate
34. anhydro-2-methyl-1-(3-sulfopropoxy)pyridinium hydroxide
35. 1-ethoxy-2-methylpyridinium tetrafluoroborate
36. 1-benzyloxy-2-methylpyridinium bromide
37. 1-ethoxy-2-methylquinolinium tetrafluoroborate
38. 1-methoxy-2-phenylindole
39. 1-ethoxy-2-phenylindole
40. 1'-methoxy-1,3,3-trimethyl-5-nitro-2'-phenylindo-3'-indolocarbocyanine perchlorate
41. 1-methoxy-1',3',3'-trimethyl-2-phenyl-3-indolo-2'-pyrrolo[2,3-b]pyridocarbocyanine perchlorate
42. 1'-ethoxy-1,3,3-trimethyl-5-nitro-2'-phenylindo-3'-indolocarbocyanine p-toluenesulfonate
43. 1-ethoxy-1',3',3'-trimethyl-2-phenyl-3-indolo-pyrrolo-[2,3-b]pyridocarbocyanine perchlorate
44. 1,1'-ethylenedioxybispyridinium dibromide
45. 1,1'-trimethylenedioxybispyridinium dibromide
46. 1,1'-tetramethylenedioxybis(2-methylpyridinium) dibromide
47. 1,1'-tetramethylenedioxybis(4-methylpyridinium) dibromide
48. 1,1'-tetramethylenedioxybispyridinium dibromide
49. 1,1'-pentamethylenedioxybispyridinium dibromide
50. 1-methoxy-2-phenylindole-3-carboxaldehyde
51. 1-ethoxy-2-phenylindole-3-carboxaldehyde
52. 1-acetoxy-2-(4-dimethylaminostyryl)pyridinium perchlorate
53. 1-benzoyloxy-2-(4-dimethylaminostyryl)pyridinium perchlorate
54. 1,3-diethyl-5-[(1-methoxy-2(1H)-pyridylidene)-ethylidene]-2-thiobarbituric acid
55. 3-ethyl-5-[(1-methoxy-2(1H)-pyridylidene)ethylidene]rhodanine
56. 1,3-diethyl-5-[(1-methoxy-2(1H)-pyridylidene) ethylidene]barbituric acid
57. 2-(3,3-dicyanoalkylidene)-1-methoxy-1,2-dihydropyridine
58. 2-[(1-methoxy-2(1H)-pyridylidene)-ethylidene] benzo-[b]thiophen-3-(2H)-one-1,1-dioxide
59. 3-cyano-5-[(1-methoxy-2(1H)-pyridylidene)ethylidene]-4-phenyl-2(5H)-furanone The novel compounds of this invention are prepared by various methods. The following examples demonstrate some of the techniques that can be used. Indicated melting points are ° C.

EXAMPLE 1

Preparation of Compound 32 (Method A)

A mixture of 2-picoline-N-oxide (10.9 g., 0.1 mole) and methyl p-toluenesulfonate (27.9 g., 0.1 mole+50 percent) is heated on a steam bath, with constant stirring, until an exothermic reaction starts. The heating is stopped and the temperature rises to a maximum of about 120°. The mixture is allowed to cool, diluted to 200 ml. with acetone and chilled. The solid which separates is collected and washed with acetone. The yield is 23.2 g. (79 percent), m.p. 113–4° C.

EXAMPLE 2

Preparation of Compound 36 (Method B)

2-Picoline-N-oxide (10.9 g., 0.1 mole) and benzyl bromide (18.8 g., 0.1 mole+10 percent) are dissolved in acetone (25 ml.) and the mixture is heated at reflux for 10 minutes. After dilution to 150 ml. with acetone, the mixture is allowed to cool. The solid precipitate is collected and washed with acetone. The yield is 19.0 g. (68 percent), m.p. 113–4°.

EXAMPLE 3

Preparation of Compound 26

Compound 32 (5.90 g., 0.02 mole) and ethyl isoformanilide (2.98 g., 0.02 mole) in dimethyl formamide (5 ml.) are heated on a steam bath for one-half hour. The mixture is diluted with acetone (50 ml.) and chilled. The yellow solid which separates is collected and washed with acetone. The yield is 3.3 g. (41 percent), m.p. 172–3°.

EXAMPLE 4

Preparation of Compound 1

3-Ethyl-1'-methoxyoxa-2'-pyridocarbocyanine perchlorate

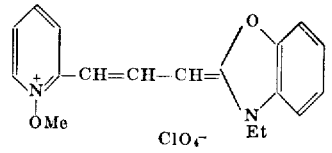

1 - Methoxy - 2 - methylpyridinium p-toluenesulfonate (2.22 g., 1 mol.+50 percent), 2-β-acetanilidovinyl-3-ethylbenzoxazolium iodide (2.17 g., 1 mol.) and triethylamine (1.4 ml., 1 mol.+100 percent) in ethanol (20 ml.) are heated at reflux for 2 minutes. Then a solution of sodium perchlorate (0.61 g., 1 mol.) in hot methanol is added. After chilling, the solid is collected and washed with ethanol. Yield 1.50 g. (77 percent), m.p. 146–7°.

EXAMPLE 5

Preparation of Compound 3

3'-Ethyl-1-methoxy-2-pyridothiacyanine iodide

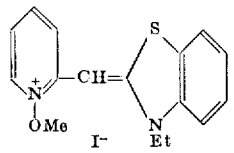

1 - Methoxy - 2 - methylpyridinium p-toluenesulfonate (4.44 g., 1 mol.+50 percent), 3-ethyl-2-phenylthiobenzothiazolium iodide (4.00 g., 1 mol.) and triethylamine (2.8 ml., 1 mol.+100 percent) in ethanol (20 ml.) are heated at reflux for 10 seconds. After chilling, the solid is collected and washed with ethanol. Yield 1.55 g. (38 percent), m.p. 159–60°.

EXAMPLE 6

Preparation of Compound 6

3'-Ethyl-1-methoxy-2-pyridothiacarbocyanine iodine

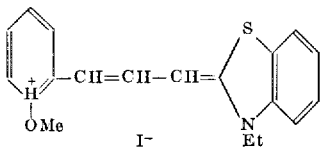

1 - Methoxy - 2 - methylpyridinium p-toluenesulfonate (2.22 g., 1 mol.+50 percent), 2-β-acetanilidovinyl-3-ethylbenzothiazolium iodide (2.25 g., 1 mol.) and triethylamine (1.4 ml., 1 mol.+100 percent) in ethanol (20 ml.) are heated at reflux for 2 minutes. The mixture is chilled and the solid which separates is collected and washed with ethanol. Yield 1.27 g. (58 percent), m.p. 115°.

EXAMPLE 7

Preparation of Compound 10

3'-Ethyl-1-methoxy-2-pyridothiadicarbocyanine perchlorate

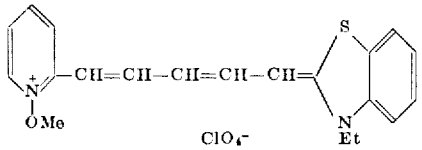

1 - Methoxy - 2 - methylpyridinium p-toluenesulfonate (3.54 g., 1 mol.+20 percent), 2-(4-acetanilido-1,3-butadienyl)-3-ethyl-benzothiazolium iodide (4.76 g., 1 mol.) and triethylamine (1.8 ml., 1 mol.+25 percent) in dimethylformamide (20 ml.) are stirred at room temperature for 2 minutes. The mixture is diluted with 400 ml. of ether. The ether layer is then decanted, the oily residue dissolved in methanol (50 ml.) and a solution of sodium perchlorate in methanol added. The mixture is cooled, the solid collected and washed with methanol. Yield 0.95 g. (22 percent).

EXAMPLE 8

Preparation of Compound 11

1'-Methoxy-1,3,3-trimethylindo-2'-pyridocarbocyanine picrate

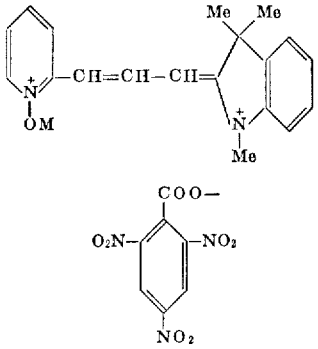

1-Methoxy-2-methylpyridinium p-toluenesulfonate (2.22 g. 1 mol.+50 percent), 2-β-acetanilidovinyl-1,3,3-trimethyl-3H-indolium iodide (2.23 g., 1 mol.), triethylamine (1.4 ml., 1 mol.+100 percent) in ethanol (20 ml.) are heated at reflux for 2 minutes. The solution is cooled and a solution of picric acid (1.15 g., 1 mol.) in ethanol added. After chilling, the solid is collected and washed with ethanol. Yield 1.12 g. (40 percent).

EXAMPLE 9

Preparation of Compound 12

3'-Ethyl-1-methoxy-4',5'-benzo-2-pyridothio carbocyanine perchlorate

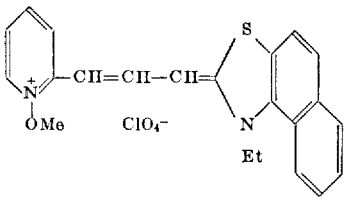

1-Methoxy-2-methylpyridinium p-toluenesulfonate (2.22 g., 1 mol.+50 percent), 2-β-anilinovinyl-1-ethylnaphtho-[1,2-d]thiazolium p-toluenesulfonate (2.57 g., 1 mol.) and triethylamine (1.4 ml., 1 mol.+100 percent) in acetic anhydride (25 ml.) are warmed to 40° and stirred for 5 minutes. The small amount of undissolved solid is removed by filtration and the filtrate diluted with excess ether. The ether layer is decanted and the residue dissolved in methanol (25 ml.). A solution of sodium perchlorate (0.61 g., 1 mol.) in methanol is added. After chilling, the solid is collected and washed with methanol. Yield 1.48 g. (65 percent), m.p. indistinct.

EXAMPLE 10

Preparation of Compound 21

1,1'-Dimethoxy-2,2'-diphenyl-3,3'-indolocarbocyanine perchlorate

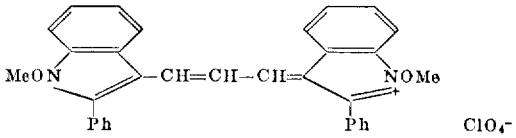

1-Methoxy-2-phenylindole (2.23 g., 2 mols.) is dissolved in hot acetic acid (10 ml.), then trimethoxypropene (2.0 g., 1 mol.+200 percent) and 48 percent HBr (1.0 ml.) are added with stirring. The mixture is allowed to cool, then diluted with excess ether. The ether layer is decanted and the viscous residue dissolved in 60 ml. MeOH, 60 percent $HClO_4$ (1.5 ml.) added, and the mixture chilled. The solid is collected and washed with methanol, water and ether. After recrystallization from methanol acidified with $HClO_4$, the yield of purified dye is 1.48 g. (52 percent), m.p. 228–30°.

EXAMPLE 11

Preparation of Compound 22

1-Methoxy-1'-methyl-2,2'-10-triphenyl-3,3'-indolocarbocyanine perchlorate

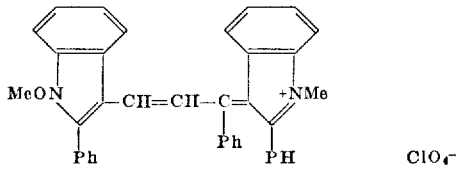

3-Formyl-1-methoxy-2-phenylindole (1.26 g., 1 mol.) and 1-methyl-2-methylenebenzyl-2-phenylindole (1.55 g., 1 mol.) are dissolved in hot acetic acid (10 ml.). 60 percent $HClO_4$ (1.0 ml.) in acetic acid (3 ml.) is added and the mixture allowed to cool. After 2 hours at room temperature, the solid is collected and washed with methanol and ether. After recrystallization from methanol acidified with $HClO_4$, the yield of purified dye is 1.92 g. (59 percent), m.p. 258–9° C.

EXAMPLE 12

Preparation of Compound 28

3'-Ethyl-1-methoxy-6'-nitro-2-phenyl-3-indolothiacarbocyanine p-toluenesulfonate

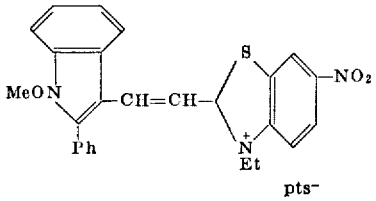

3-Formyl-1-methoxy-2-phenylindole (1.26 g., 1 mol.), 3-ethyl-2-methyl-6-nitrobenzothiazolium p - toluenesulfonate (1.98 g., 1 mol.) and acetic anhydride (10 ml.) are heated at reflux for 1 minute. After cooling, excess ether is added slowly. The solid is collected and washed with ether. After recrystallization from methanol acidified with p-toluenesulfonic acid, the yield of purified dye is 2.64 g. (84 percent).

EXAMPLE 13

Preparation of Compound 30

1,3-Diallyl-1'-methoxy-2'-phenylimidazo[4,5-b]-quinoxalino-3'-indolocarbocyanine perchlorate

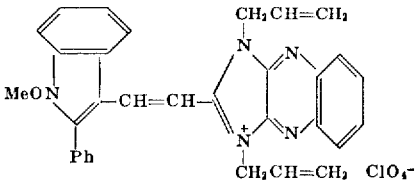

This dye is prepared in the manner described in example 12, except that 1,3-diallyl-2-methylimidazo[4,5-b]-quinoxalinium p-toluenesulfonate (2.18 g., 1 mol.) is used in place of 3 - ethyl-2-methyl-6-nitrobenzothiazolium p-toluenesulfonate. After recrystallization from a mixture of acetonitrile (65 ml.) and 60 percent $HClO_4$ (1.0 ml.), the yield of purified dye is 1.78 g. (60 percent), m.p. 229–31° C.

EXAMPLE 14

Preparation of Compound 38

1-Methoxy-2-phenylindole

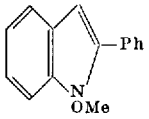

Sodium (3.0 g., 1 mol.+30 percent) is dissolved in methanol (200 ml.). 1-Hydroxy-2-phenylindole (20.9 g., 1 mol.) [Fischer, Ber. 28; 585 (1895) and Ber. 29, 2063 (1896)] and methyl iodide (25.6 g., 1 mol.+80 percent) are added, and the mixture refluxed for 1 hour. The solution is chilled, and the solid which separates is collected and washed with methanol. Yield 15.9 g. (71 percent), m.p. 51–2° C.

EXAMPLE 15

Preparation of Compound 40

1'-Methoxy-1,3,3-trimethyl-5-nitro-2'-phenylindo-3'-indolocarbocyanine perchlorate

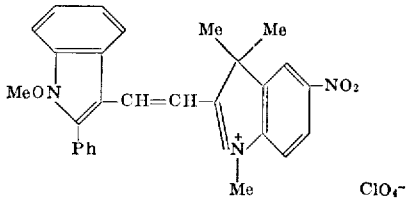

3-Formyl-1-methoxy-2-phenylindole (1.26 g., 1 mol.), 1,2,3,3 - tetramethyl-5-nitro-3H-indolium p-toluenesulfonate (1.30 g., 1 mol.) and acetic anhydride (10 ml.) are heated at reflux for 1 minute. After cooling, excess ether is added. The ether layer is decanted, the viscous residue dissolved in methanol (25 ml.) and 60 percent $HClO_4$ (1.0 ml.) in MeOH (5 ml.) added. The mixture is chilled and the solid collected and washed with methanol. After recrystallization from a mixture of methanol and acetonitrile, the yield of purified dye is 1.20 g. (43 percent), m.p. 266° C.

EXAMPLE 16

Preparation of Compound 41

1-Methoxy-1',3',3'-trimethyl-2-phenyl-3-indolo-2'-pyrrolo[2,3-b]pyridocarbocyanine perchlorate

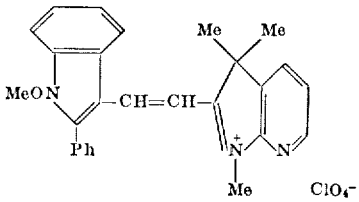

3-Formyl-1-methoxy-2-phenylindole (1.26 g., 1 mol.), 1,3,3-trimethyl-2-methylene - 2,3 - dihydropyrrolo[2,3-b] pyridine (0.87 g., 1 mol.), p-toluenesulfonic acid monohydrate (0.95 g., 1 mol.) and acetic anhydride (10 ml.) are heated at reflux for 1 minute. The mixture is allowed to cool, diluted with ether, and the ether layer decanted. The residue is dissolved in methanol (25 ml.) and 60 percent $HClO_4$ (1.0 ml.) in 5 ml. methanol added. After chilling, the solid is collected and washed with methanol. After one recrystallization from acetonitrile, the yield of purified dye is 1.78 g. (69 percent), m.p. 235–9° C.

EXAMPLE 17

Preparation of Compound 50

3-Formyl-1-methoxy-2-phenylindole

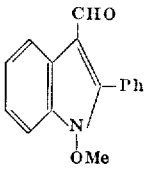

Phosphoryl chloride (5.2 ml., 1 mol.+10 percent) is added slowly to dimethyl formamide (15 ml.), with cooling, so that the temperature does not exceed 20°. A solution of 1-methoxy-2-phenylindole (11.15 g., 1 mol.) in dimethyl formamide (30 ml.) is added slowly, while keeping the temperature below 25°. The mixture is warmed at 40° for 45 minutes, then poured into ice water (390 ml.). 5N NaOH (70 ml.) is added, and a viscous mass separated. The mixture is heated to 65° and the lumps broken up. The solid is collected and washed with water. The yield is 11.95 g. (96 percent), m.p. 116–7°, unchanged after recrystallization from ethanol.

The same general methods of preparation set forth in examples 1–17 are used for the synthesis of additional compounds. The compounds prepared, method, solvent, yield and melting points for these compounds are set forth in the following tables.

TABLE I

| Ex. No. | Cpd. No. | Intermediate (Cpd. No.) | Method | Solvent | Yield (percent) | Melting point |
|---|---|---|---|---|---|---|
| 18 | 2 | 35 | Example 6 | EtOH | 43 | Decomposes. |
| 19 | 4 | 35 | Example 5 | do | 33 | Do. |
| 20 | 5 | 36 | Example 5 | do | 18 | 125–30°. |
| 21 | 7 | 35 | Example 6 | do | 89 | Decomposes. |
| 22 | 8 | 34 | Example 6 | MeOH [1] | 45 | 128–31°. |
| 23 | 9 | 36 | Example 4 | MeOH | 45 | 125°. |
| 24 | 13 | 35 | Example 9 [2] | Acetic anhydride | 81 | Decomposes. |
| 25 | 14 | 37 | Example 6 | MeOH | 38 | 143°. |
| 26 | 15 | 37 | Example 5 | MeOH | 47 | Decomposes. |
| 27 | 16 | 37 | Example 6 | MeOH | 63 | 138–9°. |
| 28 | 18 | 32 | Example 9 [3] | Acetic anhydride | 35 | 127–8°. |
| 29 | 19 | 33 | Example 5 | EtOH | 20 | 186–7°. |
| 30 | 20 | 33 | Example 4 | MeOH | 58 | 128°. |
| 31 | 23 | 39 | Example 10 | Acetic acid | 36 | 219–21°. |
| 32 | 24 | 51 | Example 11 | do | 55 | 205–9°. |
| 33 | 25 | 37 | Example 11 | $HCONMe_2(CH_3CO)_2O$ [4] | 40 | Decomposes. |
| 34 | 29 | 51 | Example 12 | Acetic anhydride | 100 | Do. |
| 35 | 31 | 51 | Example 13 | do | 58 | 220–1°. |
| 41 | 42 | 51 | Example 15 [2] | do | 65 | 194–200°. |
| 42 | 43 | 51 | Example 16 | do | 69 | 237–41°. |

[1] Reaction mixture diluted with acetone to precipitate dye.
[2] No $NaClO_4$ added.
[3] Reaction temperature 80°.
[4] Reaction temperature 25°, no $NaClO_4$ added.

TABLE II

| Ex. No. | Cpd. No. | Base | Alkylating agent | Method | Solvent | Yield (percent) | Melting point |
|---|---|---|---|---|---|---|---|
| 36 | 33 | 4-picoline-N-oxide | Methyl p-toluenesulfonate | A | | 97 | 153–4°. |
| 37 | 34 | 2-picoline-N-oxide | 1,3-propane-sultone | B | Acetone | 95 | 202–3°. |
| 38 | 35 | do | Triethyloxonium tetrafluoroborate | B | $CHCl_3$ | 80 | 53–7°. |
| 39 | 37 | Quinaldine-N-oxide | do | B | $CH_2Cl_2$ | 90 | 115–7°. |
| 40 | 39 | 1-hydroxy-2-phenylindol | Ethyl iodide | Example 14 | EtOH | 100 | Oil. |
| 43 | 44 | Pyridine-N-oxide | 1,2-dibromo-ethane | A | | 81 | 170–1°. |
| 44 | 45 | do | 1,3-dibromo-propane | A | | 100 | 151–3°. |
| 45 | 46 | 2-picoline-N-oxide | 1,4-dibromo-butane | A | | 88 | 153–4°. |
| 46 | 47 | 4-picoline-N-oxide | do | B | $CH_3CN$ | 39 | 109–11°. |
| 47 | 48 | Pyridine-N-oxide | do | A | | 91 | 172°. |
| 48 | 49 | do | 1,5-dibromo-pentane | A | | 88 | 115–7°. |
| 49 | 51 | 1-ethoxy-2-phenylindole | | Example 17 | | 98 | 95–6°. |

EXAMPLE 50

1,3-Diethyl-5-[(1-methoxy-2(1H)-pyridylidene)-ethylidene]-2-thiobarbituric acid

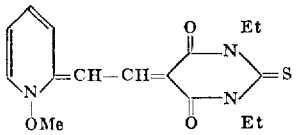

2-β-anilinovinyl-1-methoxypyridinium p - toluenesulfonate (3.99 g., 1 mol.) 1,3-diethyl-2-thiobarbituric acid (2.00 g., 1 mol.) and acetic anhydride (20 ml.) are stirred together as triethylamine (5 ml.) is added. The mixture is stirred for a few minutes until all the solid is dissolved. A seed crystal is added [obtained by dilution of a small portion of reaction mixture with excess ether] and the mixture chilled a few hours. The solid dye is collected and washed, first with methanol, then with ether. The yield of dye is 1.48 g. (44 percent), m.p. 171–2° dec.

The following compounds are prepared in the same manner as compound 54 in example 50. The compound prepared, yield and melting points are set forth in table III below.

TABLE III

| Example No. | Compound No. | Yield (percent) | Melting point (° C.) |
|---|---|---|---|
| 51 | 55 | 47 | 755 |
| | 56 | 25 | 154–5 |
| | 57 | 73 | Decomposes |
| 54 | 58 | 79 | 169–70 |
| | 59 | 88 | 1334 |

In order to provide a better understanding of the many facets of the invention, several applications will be discussed in detail. While the novel compounds described hereinbefore are useful in the various embodiments set forth below, preferred ones are described.

SENSITIZERS FOR DIRECT POSITIVE TYPE PHOTOGRAPHIC SILVER HALIDE EMULSIONS

It has been found that cyanine dyes derived from 1-alkoxy-2-arylindoles are outstanding electron acceptors and spectral sensitizers for direct positive type photographic silver halide emulsions. They provide superior reversal systems, especially with fogged silver halide emulsions, that are characterized by both good speed and desired sensitivity to radiation in the green to red region of the spectrum with maximum sensitivity occurring in most cases in the region of about 530–670 nm. The images produced with the novel direct positive emulsions of the invention are clear and sharp, and of excellent contrast.

The new class of cyanine dyes of the invention includes: those comprising first and second 5- to 6-membered nitrogen containing heterocyclic nuclei joined by a methine linkage; the first of these nuclei being a 1-alkoxy-2-arylindole nucleus joined at the 3-carbon atom thereof to the linkage; and the second nucleus being a desensitizing nucleus joined at a carbon atom thereof to the linkage, to complete the cyanine dye. The methine linkage preferably contains from 2 to 3 carbon atoms in the chain, i.e., a dimethine linkage, or a trimethine linkage which may also contain at least one side chain group.

The preferred class of novel cyanine dyes of the invention include those defined by the following formulas:

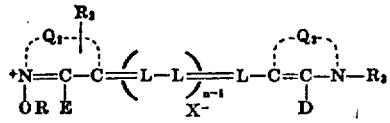

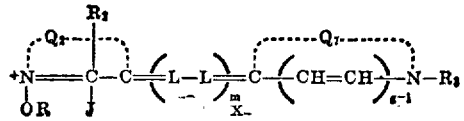

wherein:

$Q_2$ represents the atoms necessary to complete an indole nucleus;

E and J are aryl radicals, e.g., phenyl, naphthyl, tolyl, chlorophenyl, etc.;

R is an alkyl group, including substituted alkyl (preferably a lower alkyl containing from 1 to 3 carbon atoms), e.g., methyl, ethyl, propyl, isopropyl, butyl, hexyl, cyclohexyl, decyl, dodecyl, etc., and substituted alkyl groups (preferably a substituted lower alkyl containing from 1 to 4 carbon atoms);

$Q_3$, $Q_7$, D, $R_2$, n, m, g, X, L and $R_3$ are the same as previously described.

Typical representative dyes particularly suited for this portion of the invention include compounds 21–24, 28–31 and 40–43 described above.

The cyanine dyes of the invention defined above are powerful electron acceptors for direct positive photographic silver halide emulsions. In addition, they are also useful desensitizers in emulsions used in the process described in Stewart and Reeves, U.S. Pat. No. 3,250,618, issued May 10, 1966.

As used herein and in the appended claims, "desensitizing nucleus" refers to those nuclei which, when converted to a symmetrical carbocyanine dye and added to gelatin silver chlorobromide emulsion containing 40 mole percent chloride and 60 mole percent bromide, at a concentration of from 0.01 to 0.2 gram of dye per mole of silver, cause (by electron trapping) at least about an 80 percent loss in the blue speed of the emulsion when sensitometrically exposed and developed three minutes in Kodak developer D–19 at room temperature. Advantageously, the desensitizing nuclei are those which, when converted to a symmetrical carbocyanine dye and tested as just described essentially completely desensitize the test emulsion to blue radiation (i.e., cause more than about 90 to 95 percent loss of speed to blue radiation).

In accordance with one aspect of the invention, novel and improved direct positive photographic silver halide emulsions are prepared by incorporating one or more of the cyanine dyes described above into a suitable fogged silver halide emulsion. The emulsion can be fogged in any suitable manner, such as by light or with chemical fogging agents, e.g., stannous chloride, formaldehyde, thiourea dioxide, and the like. The emulsion may be fogged by the addition thereto of a reducing agent, such as thiourea dioxide, and a compound of a metal more electropositive than silver, such as a gold salt, for example, potassium chloroaurate, as described in British Pat. No. 723,019 (1955).

Among the direct positive emulsions which may be used are solarizing silver halide emulsions. These emulsions are silver halide emulsions which have been effectively fogged either chemically or by radiation, to a point which corresponds approximately to the maximum density of the reversal curve as shown by Mees, The Theory of the Photographic Process, published by MacMillan Co., New York, New York, 1042, pages 261–297.

Typical methods for the preparation of solarizing emulsions are shown by Groves British Pat. No. 443,245, Feb. 25, 1936 who subjected an emulsion to Roentgen rays "until the emulsion layer, when developed without additional exposure, is blackened up to the apex of its gradation curve"; Szaz British Pat. No. 462,730, Mar. 15, 1937, the use of either light or chemicals such as silver nitrate, organic sulfur compounds and dyes to convert ordinary silver halide emulsions to solarizing direct positive emulsions; Arens U.S. Pat. No. 2,005,837, June 25, 1935, the use of silver nitrate and other compounds in conjunction with heat to effect solarization of the silver halide, and Leermakers U.S. Pat. No. 2,184,013 and the use of large concentrations of nonacid spectral sensitizing dyes and reducing agents to effect solarization.

Kendalls and Hill U.S. Pat. No. 2,541,472, Feb. 13, 1951, shows useful solarizing emulsions particularly susceptible to an exposure with long wavelength light to produce a Herschel effect described by Mees above, produced by adding nitro substituted electron acceptors and other compounds to the emulsion which is fogged either chemically or with white light. In using the emulsions, a sufficient reversal image exposure is employed using minus blue light of from about 500–700 millimicrons wavelengths, preferably 520–540 millimicrons, to substantially destroy the latent image in the silver halide grains in the region of the image exposure.

Conventional silver halide developing solutions can be used to develop a direct positive image in solarizing emulsions.

The concentration of added dye can vary widely, e.g., from about 50 to 2,000 mg. and preferably from about 400 to 800 mg. per mole of silver halide in the direct positive emulsions.

The compounds of this invention are also advantageously incorporated in direct positive emulsions of the type in which a silver halide grain has a water-insoluble silver salt center and an outer shell composed of a fogged water-insoluble silver salt that develops to silver without exposure. The compounds of the invention are incorporated, preferably, in the outer shell of such emulsions. These emulsions can be prepared in various ways, such as those described in Berriman U.S. Pat. No. 3,367,778 issued Feb. 6, 1968.

These compounds are highly useful electron acceptors in high speed direct positive emulsions comprising fogged regular grain monodispersed silver halide grains and a compound which accepts electrons, as described and claimed in Illingsworth Belgian Pat. No. 695,366 of Sept. 11, 1967.

The silver halides employed in the preparation of the direct positive photographic emulsions useful herein include any of the photographic silver halides as exemplified by silver bromide, silver iodide, silver chloride, silver chlorobromide, silver bromoiodide, silver chlorobromide, and the like. Silver halide grains having an average grain size less than about one micron, preferably less than about 0.5 micron, give particularly good results. The silver halide grains can be regular and can be any suitable shape such as cubic or octahedral, as described and claimed in Illingsworth Belgian Pat. No. 695,366 of Sept. 11, 1967. Such grains have a uniform diameter frequency distribution. For example, at least 95 percent, by weight, of the photographic silver halide grains can have a diameter which is within about 40 percent, preferably within about 30 percent of the mean grain diameter. Mean grain diameter, i.e., average grain size, can be determined using conventional methods, e.g., as shown in an article by Trivelli and Smith entitled "Empirical Relations Between Sensitometric and Size-Frequency Characteristics in Photographic Emulsion Series" in The Photographic Journal, Vol. LXXIX, 1949, pages 330–338.

In the preparation of the above direct positive photographic emulsions, the compounds of the invention are advantageously incorporated in the washed, finished silver halide emulsion and should, of course, be uniformly distributed throughout the emulsion. The methods of incorporating such compounds and other addenda in emulsions are relatively simple and well known to those skilled in the art of emulsion making. For example, it is convenient to add them from solutions in appropriate solvents, in which case the solvent selected should be completely free from any deleterious effect on the ultimate light-sensitive materials. Methanol, isopropanol, pyridine, water, etc., alone or in admixtures, have proven satisfactory as solvents for this purpose. The type of silver halide emulsions that can be used with these compounds include any of those prepared with hydrophilic colloids that are known to be satisfactory for dispersing silver halides, for example, emulsions comprising natural materials such as gelatin, albumin, agar-agar, gum arabic, alginic acid, etc., and hydrophilic synthetic resins such as polyvinyl alcohol, polyvinyl pyrrolidone, cellulose ethers, partially hydrolyzed cellulose acetate, and the like.

The compounds of the invention can be used with emulsions prepared, as indicated above, with any of the light-sensitive silver halide salts including silver chloride, silver bromide, silver chlorobromide, silver bromoiodide, silver chlorobromoiodide, etc. Particularly useful are direct positive fogged emulsions in which the silver salt is a silver bromohalide comprising more than 50 mole percent bromide. Certain compounds of this invention are also useful in emulsions which contain color formers.

The novel emulsions of this invention may be coated on any suitable photographic support, such as glass, film base such as cellulose acetate, cellulose acetate butyrate, polyesters such as poly(ethylene terephthalate), polystyrene, paper, baryta coated paper, polyolefin coated paper, e.g., polyethylene or polypropylene coated paper, which can be electron bombarded to promote emulsion adhesion, to produce the novel photographic elements of the invention.

EXAMPLE 56

1,1′ - Dimethoxy - 2,2′ - diphenyl-3,3′-indolocarbocyanine perchlorate is photographically tested for its usefulness as an electron acceptor and spectral sensitizer for fogged direct positive photographic silver halide emulsions by the following procedure. A regular grain monodispersed silver bromoiodide gelatin emulsion (2.5 mole percent of the halide being iodide) and having an average grain size of about 0.2 micron is prepared by adding an aqueous solution of potassium bromide and potassium iodide, and an aqueous solution of silver nitrate, simultaneously to a rapidly agitated aqueous gelatin solution at a temperature of 70° C., over a period of about 35 minutes. The emulsion is chill-set, shredded and washed by leaching with cold water in the conventional manner. The emulsion is reduction-gold fogged by first adding 0.2 mg. of thiourea dioxide per mole of silver and heating for 60 minutes at 65° C. and then adding 4.0 mg. of potassium chloroaurate per mole of silver and heating for 60 minutes at 65° C. The above dye, is then added to the above fogged emulsion in amount sufficient to give a concentration as indicated in table III hereinafter, of the dye per mole of silver. The resulting emulsion is then coated on a cellulose acetate film support at a coverage of 100 mg. of silver and 400 mg. of gelatin per square foot of support. A sample of the coated support is then exposed on an Eastman IB sensitometer using a tungsten light source and processed for 6 minutes at room temperature in Kodak D–19 developer which has the following composition:

| | G. |
|---|---|
| N-methyl-p-aminophenol sulfate | 2.0 |
| Sodium sulfite (anhydrous) | 90.0 |
| Hydroquinone | 8.0 |
| Sodium carbonate (monohydrate) | 52.5 |
| Potassium bromide | 5.0 |
| Water to make 1.0 liter. | |

then fixed, washed and dried. The results are listed in table IV hereinafter. Referring thereto, it will be seen that the dye of this example has a maximum density in the unexposed areas of 1.38 and a minimum density in exposed areas of 0.02, a maximum sensitivity at 650 nm. and a relative speed of 3,630, whereas the control sample similarly prepared and tested but containing no spectral sensitizing dye shows no reversal and has a relative speed less than 1. This result indicates that the dye compound of the above example is especially well suited to function as a spectral sensitizer. It thus provides excellent quality direct positive photographic silver halide emulsions. Excellent magenta images are obtained when the color former 1-(2,4,6-trichlorophenyl) - 3,3′ - (2″,4″-di - t - amylphenoxyacetamido)-benzamido-5-pyrazolone is incorporated in the emulsion of this example, the emulsion coated on a support, exposed to a tungsten source through Wratten filter No. 61 and No. 16, and reversal processed as described in Graham et al. U.S. Pat. No. 3,046,129, issued July 24, 1962, in example (a) Col 27, line 27 et seq. except that black-and-white (metal-hydroquinone) development is omitted, the color development is reduced to one minute and is conducted in total darkness until after fixing.

EXAMPLE 57

Compound 22 is tested for reversal and sensitizing properties by the procedure described in above example 56. The results are recorded in table IV hereinafter. Referring to the table, densities of 1.70 and 0.03 for the unexposed and exposed areas, respectively, a maximum sensitivity at 660 nm. and a relative speed of 3,800 are shown for this dye. Accordingly, the above prepared dye is an excellent electron acceptor and spectral sensitizer for fogged direct positive emulsions.

EXAMPLE 58

Compound 28 is tested for reversal and sensitizing properties by the procedure described in above example 56 The results are recorded in table IV hereinafter. Referring thereto, it will be noted that the densities are 1.46 and 0.06 for the unexposed and exposed areas, respectively, with a maximum sensitivity at 575 nm., and a relative speed of 3,020. These results indicate that this dye is an outstanding electron acceptor and spectral sensitizer for fogged direct positive emulsions.

The effectiveness of these and other dyes of this portion of the invention as electron acceptors and spectral sensitizers for fogged direct positive photographic silver halide emulsions is recorded in the following table. The test procedure is described in above example 56.

TABLE IV

| | | Density | | | |
|---|---|---|---|---|---|
| Dye No. | Dye conc., g./mole silver | Relative clear speed | Max. unexposed areas | Min. exposed areas | Sensitizing max. (nm.) |
| 21 | 0.70 | 3,630 | 1.38 | 0.02 | 650 |
| 22 | 0.90 | 3,800 | 1.70 | 0.03 | 660 |
| 28 | 0.70 | 3,020 | 1.46 | 0.06 | 575 |
| 30 | 0.70 | 3,310 | 1.36 | 0.02 | 565 |
| 40 | 0.60 | 3,310 | 1.50 | 0.04 | 575 |
| 41 | 0.70 | 2,630 | 1.59 | 0.01 | 540 |
| Control | 0.00 | <1 | 1.90 | No reversal | |

The following examples further illustrate the preparation of fogged direct positive emulsions and elements with the compounds of the invention.

EXAMPLE 59

To one mole of a silver chloride gelatin emulsion containing an equivalent of 100 grams of silver nitrate is added 0.029 gram of compound 21. The emulsion is coated on a nonglossy paper support, and is flashed with white light to give a density of 1.2 when developed in the following developer, diluted 1 part to 2 parts of water:

| | G. |
|---|---|
| N-methyl-p-aminophenol sulfate | 3.1 |
| Sodium sulfite, des. | 45 |
| Hydroquinone | 12 |
| Sodium carbonate, des. | 67.5 |
| Potassium bromide | 1.9 |
| Water to 1 liter. | |

The light fogged material thus obtained can be exposed to an image with light modulated by a Wratten No. 15 filter to give a direct positive image. Similar results are obtained when compounds 22, 28, 30, 40 and 41 are substituted for the aforementioned compound of this example.

EXAMPLE 60

One mole of a silver chloride gelatin emulsion is heated to 40° C. and the pH is adjusted to 7.8. Fourteen ml. of (40 percent) formalin solution is then added and the emulsion is held at 40° C. for 10 minutes. At the end of the holding period, the pH is adjusted to 6.0 and 0.21 g. of compound 28 is incorporated therein. The emulsion is then coated on a support, and the element so obtained provides good direct positive images. Similar results are obtained when compounds 21, 22, 30, 40 and 41 are used in place of the dye of this example.

By substituting other compounds of the invention as defined by formulas I and II above, into the procedure of example 56 similar fogged, direct positive photographic silver halide emulsions and photographic elements containing such novel emulsions may be prepared.

The photographic silver halide emulsion and other layers present in the photographic elements made according to the invention can be hardened with any suitable hardener, including aldehyde hardeners such as formaldehyde, and mucochloric acid, aziridine hardeners, hardeners which are derivatives of dioxane, oxypolysaccharides such as oxy starch or oxy plant gums, and the like. The emulsion layers can also contain additional additives, particularly those known to be beneficial in photographic emulsions, including, for example, lubricating materials, stabilizers, speed increasing materials, absorbing dyes, plasticizers, and the like. These photographic emulsions can also contain in some cases additional spectral sensitizing dyes. Furthermore, these emulsions can contain color forming couplers or can be developed in solutions containing couplers or other color generating materials. Among the useful color formers are the monomeric and polymeric color formers or couplers, e.g., 5-pyrazolone, phenolic and open chain couplers having a reactive methylene group. The color forming couplers can be incorporated into the direct positive photographic silver halide emulsion using any suitable technique, e.g., techniques of the type shown in Jelley et al. U.S. Pat. No. 2,322,027, issued June 15, 1943, Fierke et al. U.S. Pat. No. 2,801,-171, issued July 30, 1957, Fisher U.S. Pat. Nos. 1,055,155 and 1,102,028, issued Mar. 4, 1913 and June 30, 1914, respectively, and Wilmanns U.S. Pat. No. 2,186,849, issued Jan. 9, 1940. They can also be developed using incorporated developers such as polyhydroxybenzenes, aminophenols, 3-pyrazolidones, and the like.

Silver halide emulsions containing the compounds of this invention can be dispersed in any of the binders disclosed and referred to in Beavers U.S. Pat. No. 3,039,873, issued June 19, 1962, col. 13, or polymerized vinyl compounds such as those disclosed in U.S. Pat. Nos. 3,142,-568; 3,193,386; 3,062,674; and 3,220,844, and including the water insoluble polymers of alkyl acrylates and methacrylates, acrylic acid, sulfoalkyl acrylates or methacrylates and the like.

SENSITIZERS FOR NEGATIVE TYPE PHOTOGRAPHIC SILVER HALIDE EMULSIONS

According to this aspect of the invention, cyanine dyes derived from 1-alkoxypyridines and 1-alkoxyquinolines are useful spectral sensitizers for negative-type photographic silver halide emulsions. They provide emulsions that are characterized by both good speed and desired sensitivity to radiation in the green to red region of the spectrum with maximum sensitivity occurring in most cases in the region of about 520–620 nm. The images produced with these novel emulsions of the invention are clear and sharp, and of excellent contrast.

This new class of cyanine dyes includes those comprising a first and a second 5 to 6 membered nitrogen-containing heterocyclic nucleus joined by a methine linkage; the first of these nuclei being either a 1-alkoxypyridyl nucleus or a 1-alkoxyquinolyl nucleus, each of these nuclei being joined at the 2-carbon atom thereof to the linkage. The second nucleus is a heterocyclic nucleus of the type commonly contained in cyanine dyes and is joined at a carbon atom to the above-mentioned methine linkage, to complete the cyanine dye. The methine linkage preferably contains one or three carbon atoms in the methine chain.

The preferred class of novel cyanine dyes of the invention include those defined by the following formula:

III

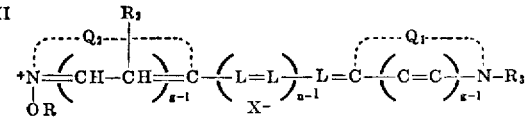

wherein:

$Q_2$ is either a pyridine nucleus or a quinoline nucleus;

R is an alkyl group, including substituted alkyl (preferably a lower alkyl containing from one to four carbon atoms), e.g., methyl, ethyl, propyl, isopropyl, butyl, hexyl, cyclohexyl, decyl, benzyl, dodecyl, etc.; an aryl group, e.g., phenyl, naphthyl, tolyl, chlorophenyl, etc.; or an acyl group, e.g., acetyl.

$R_2$, L, $R_3$, $Q_1$, X, g and n have previously been defined.

Typical representative dye salts best suited for this portion of the invention include compounds 1–20, 25 and 27 of table I.

As referred to herein and in the appended claims the term "heterocyclic nucleus of the type commonly contained in cyanine dyes" includes any of the following nuclei: the thiazole series (e.g., thiazole, 4-methylthiazole, 5-methylthiazole, 4-phenylthiazole, 5-phenylthiazole, 4,5-dimethylthiazole, 4,5-diphenylthiazole, 4-(2-thienyl) thiazole, etc.), those of the benzothiazole series (e.g., benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 4-phenylbenzothiazole, 5-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, a tetrahydrobenzothiazole nucleus, 5,6-dimethoxybenzothiazole, 5,6-dioxymethylenebenzothiazole, 5-hydroxybenzothiazole, 6-hydroxybenzothiazole, etc.), those of the naphthothiazole series (e.g., α-naphthothiazole (i.e., [2,1]-naphthothiazole), β-naphthothiazole (i.e., [1,2]-naphthothiazole), 5-methoxy-β-naphthothiazole, 5-ethoxy-β-naphthothiazole, 7-methoxy-α-naphthothiazole, 8-methoxy-α-naphthothiazole, etc.), those of the thianaphtheno-7′,6′,4,5-thiazole series (e.g., 4′-methoxythianaphtheno-7′,6′,4,5-thiazole, etc.), those of the oxazole series (e.g., 4-methyloxazole, 5-methyloxazole, 4-phenyloxazole, 4,5-diphenyloxazole, 4-ethyloxazole, 4,5-dimethyloxazole, 5-phenyloxazole, etc.), those of the benzoxazole series (e.g., benzoxazole, 5-chlorobenzoxazole, 5-phenylbenzoxazole, 5-methylbenzoxazole, 6-methylbenoxazole, 5,6-dimethylbenzoxazole, 4,6-dimethylbenzoxazole, 5-methoxybenzoxazole, 6-methoxybenzoxazole, 5-ethoxybenzoxazole, 6-chlorobenzoxazole, 5-hydroxybenzoxazole, 6-hydroxybenzoxazole, etc.), those of the naphthoxazole series (e.g., α-naphthoxazole, β-naphthoxazole, etc.), those of the selenazole series (e.g., 4-methylselenazole, 4-phenylselenazole, etc.), those of the benzoselenazole series (e.g., benzoselenazole, 5-chlorobenzoselenazole, 5-methoxybenzoselenazole, 5-hydroxybenzoselenazole, a tetrahydrobenzoselenazole nucleus, etc.), those of the naphthoselenazole series (e.g., α-naphthoselenazole, β-naphthoselenazole, etc.), those of the thiazoline series (e.g., thiazoline, 4-methylthiazoline, etc.), those of the 2-quinoline series (e.g., quinoline, 3-methylquinoline, 5-methylquinoline, 7-methylquinoline, 8-methylquinoline, 6-chloroquinoline, 8-chloroquinoline, 6-methyoxyquinoline, 6-ethoxyquinoline, 6-hydroxyquinoline, 8-hydroxyquinoline, etc.), those of the 4-quinoline series (e.g., quinoline, 6-methoxyquinoline, 7-methylquinoline, 8-methylquinoline, etc.), those of the 1-isoquinoline series (e.g., isoquinoline, 3,4-dihydroisoquinoline, etc.), those of the 3,3-dialkylindolenine series (e.g., 3,3-dimethylindolenine, 3,3,5-trimethylindolenine, 3,3,7-trimethylindolenine, etc.), those of the 2-pyridine series (e.g., pyridine, 3-methylpyridine, 4-methylpyridine, 5-methylpyridine, 6-methylpyridine, 3,4-dimethylpyridine, 3,5-dimethylpyridine, 3,6-dimethylpyridine, 4,5-dimethylpyridine, 4,6-dimethylpyridine, 4-chloropyridine, 5-chloropyridine, 6-chloropyridine, 3-hydroxypyridine, 4-hydroxypyridine, 5-hydroxypyridine, 6-hydroxypyridine, 3-phenylpyridine, 4-phenylpyridine, 6-phenylpyridine, etc.) those of the 4-pyridine series (e.g., 2-methylpyridine, 3-methylpyridine, 2-chloropyridine, 3-chloropyridine, 2,3-dimethylpyridine, 2,5-dimethylpyridine, 2,6-dimethylpyridine, 2-hydroxypyridine, 3-hydroxypyridine, etc.), etc.

Sensitization by means of these new dyes is particularly useful with the ordinarily employed negative speed, gelatino-silver halide developing-out emulsions. The dyes are advantageously incorporated in the emulsion and should be uniformly distributed throughout the emulsion. The methods of incorporating dyes in the emulsion are simple and well known to those skilled in the art of emulsion making. It is convenient to add the dyes from solutions in appropriate solvents. The solvent should be compatible with the emulsion and substantially free from any deleterious effect on the light-sensitive materials.

The concentration of the dyes in the negative-type, developing-out emulsions can vary widely, i.e., from about 5 to about 100 mgs. per liter of flowable emulsion. The concentration of the dye will vary according to the type of light-sensitive material in the emulsion and according to the effects desired. The suitable and most economical concentration for any given emulsion will be apparent to those skilled in the art upon making the ordinary tests and observations customarily used in the art of emulsion making.

To prepare a negative speed, gelatino-silver halide developing-out emulsion sensitized with one of these dyes, the following procedure is satisfactory. A quantity of the dye is dissolved in methyl alcohol or other suitable solvent and a volume of this solution (which may be diluted with water) containing from 5 to 100 mgs. of dye is slowly added to about 1,000 cc. of a gelatino-silver halide emulsion, with stirring. Stirring is continued until the dye is uniformly distributed throughout the emulsion. With most of the dyes, 10 to 20 mgs. of dye per liter of emulsion suffices to produce the maximum sensitizing effect with the ordinary gelatino-silver bromide (including bromoiodide) emulsions. With fine-grain emulsions, which include most of the ordinarily employed gelatino-silver chloride emulsions, somewhat larger concentrations of dye may be necessary to secure the optimum sensitizing effect.

The above statements are only illustrative and are not to be understood as limiting this portion of the invention in any sense, as it will be apparent that these dyes can be incorporated by other methods in many of the photographic silver halide emulsions customarily employed in the art. For instance, the dyes can be incorporated by bathing a plate or film upon which an emulsion has been coated in a solution of the dye in an appropriate solvent. Bathing methods, however, are not to be preferred ordinarily.

Photographic silver halide emulsions which can advantageously be sensitized by means of the new dyes of the invention comprise the customarily employed silver chloride, silver chlorobromide, gelatino-silver bromide, silver chlorobromoiodide and gelatino-silver bromoiodide negative-speed developing-out emulsions.

Photographic silver halide emulsions, such as those listed above, containing the sensitizing dyes can also contain such addenda as chemical sensitizers, e.g., sulfur sensitizers (e.g., allyl thiocarbamide, thiourea, allylisothiocyanate, cystine, etc.), selenium compounds, tellurium compounds, various gold compounds (e.g., potassium chloroaurate, auric trichloride, etc.) (see U.S. Pat. Nos. 2,540,085; 2,597,856 and 2,597,915), various palladium compounds, such as palladium chloride (U.S. Pat. No. 2,540,086), potassium chloropalladate (U.S. Pat. No. 2,598,079), etc., or mixtures of such sensitizers; antifoggants, such as ammonium chloroplatinate (U.S. Pat. No. 2,566,245), ammonium chloroplatinite (U.S. Pat. No. 2,566,263), benzotriazole, nitrobenzimidazole, 5-nitroindazole, benzidine, mercaptans, etc. (see Mees, "The Theory of the Photographic Process," MacMillan Pub., page 460), or mixtures thereof, hardeners, such as formaldehyde (U.S. Pat. No. 1,763,533), chrome alum U.S. Pat. No. 1,763,533), glyoxal (U.S. Pat. No. 1,870,354), dibromoacrolein (Br. 406,750), etc.; color formers or couplers, such as those described in U.S. Pat. No. 2,423,730, Spence and Carroll U.S. Pat. No. 2,640,776, etc.; or mixtures of such addenda. Dispersing agents for color couplers, such as those set forth in U.S. Pat. Nos. 2,322,027 and 2,304,940, can also be employed in the above described emulsions.

EXAMPLE 61

In order to demonstrate the sensitization which the dyes impart, a negative-speed developing-out gelatino-silver bromoiodide emulsion containing 0.77 mole percent of the type described by Trivelli and Smith, Phot. Journal, 79, 330 (1939) is prepared. Various dyes are dissolved in suitable solvents and the solution added to separate portions of the emulsion at concentrations set forth in the following table. After digestion at 52° C. for 10 minutes, the emulsions are coated at a thickness of 432 mg. of silver per square foot on a cellulose acetate film support. A sample of each coating is exposed on an Eastman IB sensitometer to a wedge spectrograph, processed for 3 minutes in Kodak Developer D–19, fixed in hypo, washed and dried. The maximum sensitivity is set forth in the following table.

| Compound No. | Concentration, g./mole | $\lambda_{max.}$ |
|---|---|---|
| 1 | 0.08 | 530 |
| 6 | 0.08 | 570 |
| 12 | 0.08 | 600 |
| Control | 0.00 | None |

EXAMPLE 62

The emulsions of Example 61 are coated on a support and the resultant elements are exposed to an image. Upon processing as described in Example 61 good quality negatives are obtained.

PHOTOBLEACH IMAGES

The dyes of the invention are useful in the production of direct positive photographic images by bleaching of such dyes. It has been found that the dyes of the invention are bleached in proportion to the exposure energy they receive. The bleaching results from the fragmentation of the dye molecule, fragmentation being caused, at least in part, by the cleavage of the N–O linkage. Thus, when the dyes are coated on or imbibed into a suitable support and exposed in an imagewise manner, direct positive reproductions are obtained. The advantages of this process are numerous, e.g., no chemical development is necessary nor is there any need for any other material in the coating composition other than the dye itself. Since the dyes of the invention are of different colors, images having various colors can be made. For coating purposes, it is often convenient to disperse the dye in a film-forming binder. Useful binders include those which are commonly used in preparing photographic elements.

While generally all of the compounds encompassed by formulas A through H are suitable in preparing photobleach images, the preferred ones have the following structure:

IV

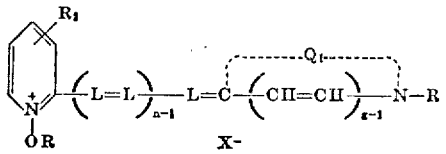

V

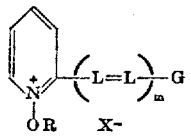

VI

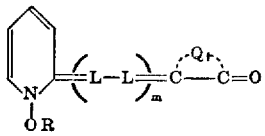

VII

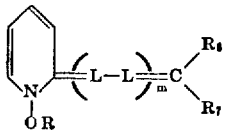

wherein:

R, $R_2$, $R_3$, $R_6$, $R_7$, L, $Q_1$, $Q_4$, X, G, n, g and m are each defined above. Typical componds exemplary of the above include compounds 1–13, 18, 26, 52 through 59.

Since these bleachable dyes are of various colors, as explained previously, they can be used in the production of direct positive color prints. Thus, when a white substrate is coated with a layer of a yellow dye, a layer of a magenta dye and a layer of a cyan dye and the resultant element is exposed to white light through a color transparency, a direct positive color print is obtained. The three dyes need not be present as separate layers but may be in a uniform admixture. The color image is obtained by virtue of the fact that these dyes are bleached when exposed to a light source of substantially the same wavelength which they absorb. Since yellow absorbs blue, where light in the blue region strikes the yellow layer, the yellow layer bleaches and becomes colorless. Similar effects are observed in the other two layers, magenta absorbing green and bleaching and cyan absorbing red and bleaching in proportions to the exposure received. The result of the process is a right-reading color reproduction of the color original. Such a process is generally known in the art, and is more fully described in U.S. Pat. No. 3,104,973(Sprague et al.).

EXAMPLE 63

A solution of 46.1 mg. of compound 12 (magenta), 43.7 mg. of compound 10 (cyan) and 39.8 mg. of compound 4 (yellow) in 50 g. of 20 percent poly-(2-vinylpyridine) binder is prepared by rotary mixing. After two hours mixing 1.46 g. of triethanolamine is added and the solution is mixed for an additional 2 hours. The solution is then coated on a white pigmented cellulose acetate base at a thickness of 0.002 in. After drying, the elements are exposed through a color positive transparency with a high intensity flash lamp. Instant color positives are obtained.

THERMOGRAPHIC COPYING

The dyes of the invention (i.e., formulas A–H) can be used to prepare thermographic copy elements. As explained previously, the compounds of this invention fragment when subjected to various forms of energy. Accordingly, when these compounds are exposed to heat, fragmentation occurs. The compounds lose their original color and generally are bleached. Because of this feature, they can be used in thermographic copy sheets as the heat-sensitive material. Dyes of formula E are preferred.

The compounds forming the heat-sensitive areas of a copy sheet can be coated on or imbibed into any suitable support (especially support having low thermal conductivity). In general, ordinary paper can be used as a support for the heat-sensitive composition and the paer can be transparent, translucent or opaque. It is frequently desirable to use a support which transmits the exposing radiation, especially where the original does not transmit such radiation (i.e., at least one of these should transmit such radiation). Advantageously, a paper or other fibrous material can be employed which has a charring temperature above about 125° C.

In preparing thermographic elements of this invention, the heat-sensitive dye is usually coated on a translucent or opaque support. After a period of drying, the heat-sensitive, copying sheet can then be placed in contact with an original containing line copy, such as typewritten characters, and exposed to infrared radiation. The portions of the original which are highly absorptive of the infrared radiation convert the radiation to heat which is conducted to the copying material producing a rapid color change in those portions of the copying sheet which are in heat-conductive relationship with the original. The portions of the copying sheet which are not in heat-conductive relationship with the original, transmit or reflect the infrared radiation so that no color change occurs.

If desired, the heat-sensitive compounds of the invention can be dispersed in a binding material and the entire composition coated on the surface of the support. Suitable binding agents include ethyl cellulose, polyvinyl alcohol, gelatin, collodion, polyvinyl acetal cellulose esters, hydrolyzed cellulose esters, etc. When a colloidal binding agent is employed, the amount thereof used can be varied in order to vary the contrast of the resulting copy. These effects are well understood by those skilled in the art. Various esthetic effects may be produced by adding inert pigments or colorants to the colloidal dispersions, although there is generally no advantage to be gained by the use of such materials. In some instances, an apparent increase in contrast can be obtained by using a coloring pigment in the colloidal binding material.

The source of infrared radiation can be arranged so that the rear surface of the original receives the infrared radiation, although in such cases it may be convenient to have an insulating surface applied to the rear surface of the original in order to localize and intensify the heat received by the original. Alternatively, the heat-sensitive layer of the copying material can be placed in contact with the printed characters of the original and the assembly then exposed either from the rear side of the original or the rear side of the copying sheet. These adaptations are well understood by those skilled in the art and are illustrated in domestic and foreign patents. See for example, Miller U.S. Pat. No. 2,663,657, issued Dec. 22, 1953.

Exposure of the thermographic element can be accomplished by reflex (as explained above) or by bireflex techniques. According to the latter method, a support for such an exposure should be readily permeable to radiant energy, such as infrared radiation. Also, the support is advantageously relatively thin so that the heat generated in the printed characters of the original can be transmitted to the heat-sensitive layer thereby causing a color change to take place in a pattern corresponding to the printed characters. If desired, the support can be ordinary paper which has been transparentized temporarily, so that exposure can be made as described. The transparentizing substance can then be removed after exposure to provide an opaque reflecting support. Such transparentizing treatment is well known to those skilled in the art.

It has also been found that the application of the heat sensitive layer to the support need not be done in a uniform manner, but that the heat-sensitive layer can be applied nonuniformly in a regular pattern, such as lines or dots. Such coatings can be used for special purposes, such as in the graphic arts field.

While only an infrared lamp has been discussed as the exposing source, it is to be understood that other sources of radiant energy can conveniently be employed in the described thermographic process. Advantageously, the source of radiation is selected so that it is strongly absorbed by the characters or printed materials being reproduced. Thus, the characters absorb the radiant energy and transform it into heat which is transmitted to the heat-sensitive coating. Incandescent bodies can conveniently be employed as the source of radiant energy, since such incandescent material is generally rich in the radiant energy absorbed by many of the printing materials currently being used. Where the radiant energy is not transmitted by the support bearing the heat-sensitive material, the material being copied should transmit such radiant energy so that exposure can be made through the rear surface of the material bearing the printed characters.

While any of the compounds within the scope of formulas A–H are operable in the novel heat-sensitive elements described herein, compounds 1–53 are preferred.

EXAMPLE 64

A paper support is coated with a layer of a composition containing gelatin and compound 12. A graphic original having printed material thereon is placed in contact with the uncoated surface of the paper. Upon exposure of the assembly to infrared radiation supplied by an infrared lamp, a facsimile copy of the printed characters of the original is obtained.

EXAMPLE 65

A composition containing compound 32 in gelatin is coated on an aluminum base. The element is written on with a hot stylus on the noncoated side. A good image is recorded in the heated areas.

LIGHT-SCREENING LAYERS

The dyes described herein have been found to be useful in light-screening layers, including antihalation and filter layers, in photographic light-sensitive elements employing one or more sensitive silver halide layers. They can be incorporated readily in colloidal binders used for forming such layers or they can be coated without the aid of a vehicle. They are especially useful in gelatin layers adjacent to the silver halide layers and also in dry processes. The dyes can be readily bleached without the need for removing the layers containing them. Bleaching of the dyes occurs when the layer containing them is subjected to some form of energy, e.g., light or heat. The energy causes the compound to fragment and become colorless, as explained previously.

These dye compounds can be mordanted in layers coated in contact with light-sensive silver halide emulsion layers since the mordanted dyes have very good stability at the pH of most sensitive silver halide emulsions and have little or no undesirable effect on the silver halide. Also, the dyes can be used as light-screening dyes in layers coated directly on top of sensitive silver halide emulsion layers or between two sensitive silver halide emulsion layers or between the support and a sensitive silver halide emulsion layer or on the back of the support as an antihalation layer. The elements in which these materials are used as screening layers can contain either the conventional developing-out silver halide emulsions or light-developable silver halide emulsions such as those described in Ser. No. 481,918, filed Aug. 23, 1965, now U.S. Pat. No. 3,418,122 and Ser. No. 625,590, filed Mar. 24, 1967, now U.S. Pat. No. 3,447,927.

The light-screeing layers of this invention are prepared by coating on the photographic element or on its support, by methods well known in the art, a solution of the dye, a hydrophilic colloid binder and a coating aid such as saponin. In addition to these materials, it is advantageous to add a mordant to this solution to render the dye nonwandering. For most purposes it is desirable to add agents to harden the colloidal binder material so that the light-screening layer wil remain intact in the photographic element during and following the processing operation. The pH of the coating solution is adjusted when necessary to a level that is compatible with the light-sensitive emulsion layer by the usual methods.

The proportions of the dye, colloidal binder, mordant, hardener, and coating aid used in making the light-screening layers can be varied over wide ranges and will depend upon the specific requirements of the photographic element being produced. The methods used to determine the optimum composition are well known in the art and need not be described here.

The light-sensitive layer or layers and the light-screening layer or layers of the photographic element can be coated on any suitable support material used in photography such as cellulose nitrate, cellulose acetate, synthetic resins, paper, metal, glass, etc.

Hydrophilic colloidal materials used as binders for light-screening dyes of the invention include gelatin, collodion, gum arabic, cellulose ester derivatives such as alkyl esters of carboxylated cellulose, hydroxy ethyl cellulose, carboxy methyl cellulose, carboxymethyl hydroxyethyl cellulose, synthetic resins, such as the amphoteric copolymers described by Clavier et al in U.S. Pat. No. 2,949,442 issued Aug. 16, 1960, polyvinyl alcohol, and others well known in the art. The above-mentioned amphoteric copolymers are made by polymerizing a monomer having the formula:

$$CH_2{=}\underset{\underset{COOH}{|}}{CR}$$

wherein R represents an atom of hydrogen or a methyl group, and a salt of a compound having the general formula:

$$CH_2{=}\underset{\underset{CH_2NH_2}{|}}{CR}$$

wherein R has the above-mentioned meaning, such as an allylamine salt. These monomers can further be polymerized with a third unsaturated monomer in an amount of 0 to 20 percent of the total monomer used, such as an ethylene monomer that is copolymerizable with the two principal monomers. The third monomer can contain neither a basic group nor an acid group and may, for example, be vinyl acetate, vinyl chloride, acrylonitrile, methacrylonitrile, styrene, acrylates, methacrylates, acrylamide, methacrylamide, etc. Examples of these polymeric gelatin substitutes are copolymers of allylamine and methacrylic acid; coploymers of allylamide, acrylic acid and acrylamide; hydrolyzed copolymers of allylamine, methacrylic acid and vinyl acetate; copolymers of allylamine, acrylic acid and styrene; the copolymer of allylamide, methacrylic acid and acrylonitrile; etc.

In preparing the light-screening layer composition, the dye is generally added to the water-permeable colloidal binder in water solution. In some instances it can be advantageous to form an alkali metal salt of the dye by dissolving the dye in a dilute aqueous alkali metal carbonate solution. Usually a coating aid, such as saponin is added to the dye colloidal suspension before coating it as a layer on the photographic element. The dye is advantageously mordanted with a suitable basic mordant added to the colloidal suspension before coating.

Mordants that can be used include the mordants described by Minsk in U.S. Pat. No. 2,822,156, issued Apr. 14, 1959, prepared by condensing a polyvinyl-oxo-compound such as a polyacrolein, a poly-γ-methylacrolein, a polyvinyl alkyl ketone such as polyvinyl methyl ketone, polyvinyl ethyl ketone, polyvinyl propyl ketone, polyvinyl butyl ketone, etc., or certain copolymers containing acrolein, methacrolein, or the above mentioned vinyl alkyl ketone components, for example, 1 to 1 molar ratio copolymers of these components with styrene or alkyl methacrylates wherein the alkyl group contains from 1 to 4 carbon atoms, such as methyl, ethyl, propyl, or butyl methacrylates in the proportions from about 0.25 to 5 parts by weight of the said polymeric oxo-compound with one part by weight of an aminoquanidine compound such as aminoguanidine bicarbonate, aminoquanidine acetate, aminoguanidine butyrate, etc.; the reaction products of polyvinylsulfonates with C-aminopyridines of Reynolds et al. U.S. Pat. No. 2,768,078, issued Oct. 23, 1956, prepared by reacting alkyl and aryl polyvinyl sulfonates prepared as described in U.S. Pat. No. 2,531,468 and U.S. Pat. No. 2,531,469 both dated Nov. 28, 1950, under controlled conditions with C-aminopyridines or alkyl group substituted C-aminopyridines such as 2-aminopyridine, 4-aminopyridine, the aminopicolines such as 2-amino-3-methylpyridine, 2-amino-4-methylpyridine, 2-amino-5-methylpyridine, 2-amino-6-methylpyridine and corresponding 4-aminomethyl derivatives which react in this reaction is exactly the same way, 2-amino-6-ethylpyridine, 2-amino-6-butylpyridine, 2-amino-6-amylpyridine, etc.; the various aminotoluidines such as, for example, 2-amino-3-ethyl-4-methylpyridine, etc.; the dialkylaminoalkyl esters of dialkylaminoalkylamides, e.g., such as those described by Carroll et al. U.S. Pat. No. 2,675,316 issued Apr. 13, 1954, prepared by reacting addition polymers containing carboxyl groups with a basic dialkylamino compound, for example, N-dialkylamine ethyl esters of polymers or copolymers containing carboxyl groups; the addition type polymers containing periodically occurring quaternary groups of Sprague et al. U.S. Pat. No. 2,548,564, issued Apr. 10, 1951, including quaternary ammonium salts of vinyl substituted azines such as vinylpyridine and its homologs such as vinyl quinoline, vinylacridine, and vinyl derivatives of other six-membered heterocyclic ring compounds containing hydrogen atoms. These addition polymers include 2-vinyl-pyridine polymer metho-p-toluenesulfonate, 4-vinyl-pyridine polymer metho-p-toluenesulfonate.

Hardening materials that can be used to advantage in the described light-screening layer include such hardening agents as formaldehyde; a halogen-substituted aliphatic acid such as mucobromic acid as described in White U.S. Pat. No. 2,089,019, issued May 11, 1937; a compound having a plurality of acid anhydride groups such as 7,8 - diphenylbicyclo(2,2,2) - 7 - octene - 2,3,5,6 - tetracarboxylic dianhydride, or a dicarboxylic or a disulfonic acid chloride such as terephthaloyl chloride or naphthalene-1,5-disulfonyl chloride as described in Allen and Carroll, U.S. Pat. Nos. 2,725,294 and 2,725,295, both issued Nov. 29, 1955; a cyclic 1,2-diketone such as cyclopentane-1,2-dione as described in Allen and Byers, U.S. Pat. No. 2,725,305, issued Nov. 29, 1955; a biester of methanesulfonic acid such as 1,2-di(methanesulfonoxy)-ethane as described in Allen and Laakso, U.S. Pat. No. 2,726,162, issued Dec. 6, 1955; 1,3-dihydroxymethylbenzimidazolyl-2-one as described in July, Knott and Pollak, U.S. Pat. No. 2,732,316, issued Jan. 24, 1956; a dialdehyde or a sodium bisulfite derivative thereof, the aldehyde groups of which are separated by 2–3 carbon atoms such as β-methyl glutaraldehyde bis-sodium bisulfite as described in Allen and Burness U.S. Pat. application Ser. No. 556,031, filed Dec. 29, 1955, now abandoned; a bis-aziridine carboxamide such as trimethylene bis(1-aziridine carboxamide) as described in Allen and Webster U.S. Pat. No. 2,950,197, issued Aug. 23, 1960; or 2,3-dihydroxydioxane as described in Jeffreys, U.S. Pat. No. 2,870,013, issued Jan. 20, 1959.

Photographic elements utilizing these novel light-screening layers have light-sensitive emulsion layers containing silver chloride, silver bromide, silver chlorobromide, silver iodide, silver bromoiodide, silver chlorobromoiodide, etc., as the light-sensitive material. The silver halide emulsions may be sensitized by any of the sensitizers commonly used to produce the desired sensitometric characteristics.

The dyes of this invention are valuable for preparing light-filtering layers for light-sensitive photographic elements containing silver halide emulsion layers. The light-filtering layers containing these dyes are used to advantage, either over the light-sensitive silver halide emulsion layers, or between the light-sensitive silver halide emulsion layer and the support, between two different light-sensitive layers, or as an antihalation backing layer.

EXAMPLE 66

A solution containing compound 12 dissolved in a mixture of dimethylformamide and methyl alcohol is added to an aqueous gelatin solution. The mixture is agitated thoroughly to ensure complete and uniform mixing. The resultant solution is coated on a film support so that each square foot of support contains 300 mg. of gelatin and 240 mg. of dye. Superimposed on the thus formed filter layer is a conventional photographic silver halide emulsion layer. After drying, the element is exposed and developed by usual techniques. A sharp image is obtained with no discoloration due to residual dye in background areas. In this example, the dye was bleached by light energy absorbed during the exposure step. When this example is repeated without compound 12, a blurred and fuzzy image is obtained because of the lack of filter protection.

EXAMPLE 67

Example 66 is repeated except the dye employed is compound 3 and the silver halide emulsion used and photographic process employed is that used in stabilized print out systems such as described in example 18 of Ser. No. 625,590 filed Mar. 24, 1967, now U.S. Pat. 3,447,927, Bacon et al. Again, a good reproduction is obtained. The bleaching in this example is caused by both light and heat energy.

HOLOGRAPHIC ELEMENTS

The dyes of this invention are useful in the preparation of holographic elements. The development of improved holograms has been carried out on a continuous basis since their introduction in 1948 by Prof. D. Gabor. A typical system for laser holograms is described in Scientific American, February 1968, Vol. 218, No. 2, p. 43. Holograms have in the past been recorded with silver halide emulsions. According to this portion of the invention the dyes described herein can be used in holographic elements to record holograms. Holograms produced in this manner have the advantage of affording higher resolution than the silver halide-based systems since the active particles are of molecular size (i.e., 10–35 A. for dye molecules vs. 500 A. for very fine-grain silver halide particles). Another advantage is that no processing is required since the dyes are photobleachable (as explained previously) and the image is recorded directly. Therefore, dimensional stability is not a problem. The replacement of silver halide with the dyes of this invention is also economically advantageous.

The holographic elements of this invention are prepared by mixing any of the dyes of this invention with a polymeric binder such as polymethacrylate, gelatin, poly (vinylalcohol), etc. The composition is coated on a support such as glass, Estar, cellulose acetate, Teflon, etc. The thickness of the coating may be varied from a few microns upward.

EXAMPLE 68

A holographic element is prepared by mixing a solution of 0.00793 g. of compound 18 in methanol (14 g.) with 36 grams of 28 percent poly(2-vinylpyridine) in methanol for about 17 hours. The resulting solution is hand coated at room temperature on 5×7 inch glass spectroscopic plates using a knife setting of 0.030 in. The coating is covered and allowed to dry slowly at room temperature.

EXAMPLE 69

A holographic element is prepared in the same manner as example 68 except compound 11 is used instead of compound 18.

EXAMPLE 70

The elements of examples 68 and 69 are used in the production of laser holograms. The system employed is similar to that described in the Scientific American article (op. cit.). A laser beam is divided by a beam splitter and directed by a combination of mirrors and lenses such that the reference beam impinges directly on the test coating while the other illuminates a ground glass object. The object used is a 1 cm. square spot of illuminated ground glass placed close to the holographic element so that the reference beam and object beam illuminate an area approximately 1¾ inches square on the coating. The exposure times range from 10–15 seconds with a 900 mw. laser. Each of the coatings produce good recordings of holographic fringes.

The invention has been described in detail with particular reference to certain preferred embodiments thereof, but it will be understood that variations and modifications can be effected within the spirit and scope of the invention as described hereinabove and as defined in the appended claims.

We claim:

1. An image-forming composition comprising [an energy-sensitive compound] *a film-forming binder and a photobleachable dye* having a formula selected from the group consisting of:

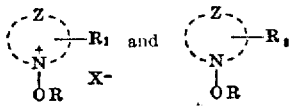

wherein:

$R_1$ is a methine terminated by a 5 to 6 membered heterocyclic nucleus, *containing carbon atoms and at least one heteroatom chosen from the class consisting of oxygen, sulfur, nitrogen, and selenium atoms;*

$R_3$ is selected from the group consisting of:

a. a methine linkage terminated by a heterocyclic nucleus of the type contained in merocyanine dyes *containing carbon atoms and at least one heteroatom chosen from the class consisting of oxygen, sulfur, nitrogen, and selenium atoms and* b. an allylidene radical;

R is selected from the group consisting of:

a. an alkyl radical and b. an acyl radical;

X is an acid anion; and

Z represents the atoms necessary to complete a 5- [to] *or* 6-membered heterocyclic nucleus *including the substituted nitrogen atom, carbon atoms and up to one or more other heteroatoms chosen from the group consisting of nitrogen, oxygen, sulfur and selenium atoms.*

2. An image-forming composition comprising [an energy-sensitive compound] *a film-forming binder and a photobleachable dye* having the formula:

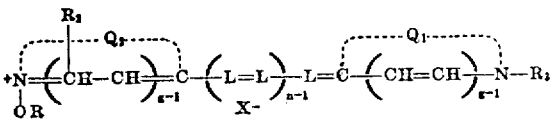

wherein:

$Q_1$ and $Q_2$ each represent the nonmetallic atoms necessary to complete a 5- to 6-membered heterocyclic nucleus *including the substituted nitrogen atom, carbon atoms and up to one or more other heteroatoms chosen from the group consisting of nitrogen, oxygen, sulfur and selenium atoms;*

R is selected from the group consisting of:

a. an alkyl radical and b. an acyl radical;

$R_2$ is selected from the group consisting of:

a. an aryl radical, b. a hydrogen atom, and c. an alkyl radical;

L is a methine linkage;

X is an acid anion;

g is a positive integer from 1 to 2;

n is a positive integer from 1 to 4; and $R_3$ is selected from the group consisting of an alkyl radical, an alkenyl radical, an aryl radical and an alkoxy radical.

3. The image-forming composition of claim 2 wherein $Q_2$ represents the atoms necessary to complete a member selected from the group consisting of a pyridine nucleus, *and* a quinoline nucleus [and an indole nucleus].

[4. An image-forming composition comprising an energy-sensitive compound having the formula:

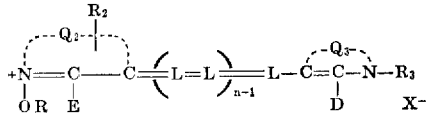

wherein:

$Q_2$ and $Q_3$ each represent the nonmetallic atoms necessary to complete a 5- to 6-membered heterocyclic nucleus;

R is selected from the group consisting of:

a. an alkyl radical, and b. an acyl radical;

$R_2$ is selected from the group consisting of:

a. an aryl radical, b. a hydrogen atom, and c. an alkyl radical;

L is a methine linkage;

X is an acid anion;

n is a positive integer from 1 to 4;

$R_3$ is selected from the group consisting of an alkyl radical, an alkenyl radical, an aryl radical and an alkoxy radical; and D and E are each selected from the group consisting of a hydrogen atom, an alkyl radical and an aryl radical.]

[5. The image-forming composition of claim 4 wherein $Q_2$ represents the atoms necessary to complete a member selected from the group consisting of a pyridine nucleus, a quinoline nucleus and an indole nucleus.]

6. An image-forming composition comprising [an energy-sensitive compound] *a film-forming binder and a photobleachable dye* having the formula:

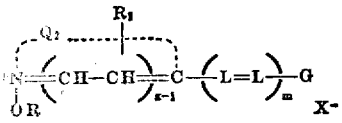

wherein:

$Q_2$ represents the atoms necessary to complete a 5- to 6-membered heterocyclic nucleus *including the substituted nitrogen atom, carbon atoms and up to one or more other heteroatoms chosen from the group consisting of nitrogen, oxygen, sulfur and selenium atoms;*

R is selected from the group consisting of:

a. an alkyl radical and b. an acyl radical;

$R_2$ is selected from the group consisting of:

a. an aryl radical, b. a hydrogen atom, and c. an alkyl radical;

L is a methine linkage;

X is an acid anion;

G is selected from the group consisting of an anilinovinyl radical and an aryl radical;

m is a positive integer from 1–3; and, g is a positive integer from 1–2.

7. The image-forming composition of claim 6 wherein $Q_2$ represents the atoms necessary to complete a member selected from the group consisting of a pyridine nucleus, *and* a quinoline nucleus [and an indole nucleus].

[8. An image-forming composition comprising an energy-sensitive compound having the formula:

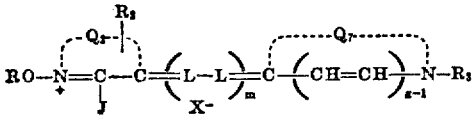

wherein:

$Q_2$ and $Q_7$ each represent the nonmetallic atoms necessary to complete a 5- to 6-membered heterocyclic nucleus;
R is selected from the group consisting of:
a. an alkyl radical and
b. an acyl radical;
$R_2$ and J are each selected from the group consisting of:
a. an aryl radical,
b. a hydrogen atom, and
c. an alkyl radical;
$R_3$ is selected from the group consisting of an alkyl radical, an alkenyl radical, an aryl radical and an alkoxy radical;
L is a methine linkage;
X is an acid anion;
*m* is a positive integer from 1 to 3; and
*g* is a positive integer from 1 to 2.]

[9. The image-forming composition of claim 8 wherein $Q_2$ represents the atoms necessary to complete a member selected from the group consisting of a pyridine nucleus, a quinoline nucleus and an indole nucleus.]

10. An image-forming element comprising a support and at least one layer of an energy-sensitive composition comprising [a compound] *a film-forming binder and a photobleachable dye* having a formula selected from the group consistinng of

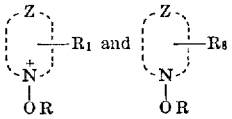

wherein:

$R_1$ is selected from the group consisting of:
a. a methine linkage terminated by a *5- or 6-membered* heterocyclic nucleus of the type contained in cyanine dyes *containing carbon atoms and at least one heteroatoms chosen from the class consisting of oxygen, sulfur, nitrogen, and selenium atoms,*
[b. an alkyl radical,]
*b.* [c.] an anilinovinyl radical,
[d. a hydrogen atom,
e. an aryl radical,
f. an aldehyde group,] and
*c.* [g.] a styryl radical;
$R_8$ is selected from the group consisting of
a. a methine linkage terminated by a *5- or 6-membered* heterocyclic nucleus of the type contained in merocyanine dyes *containing carbon atoms and at least one heteroatom chosen from the class consisting of oxygen, sulfur, nitrogen, and selenium atoms* and
b. an allylidene radical;
R is selected from the group consisting of:
a. an alkyl radical and
b. an acyl radical;
X is an acid anion, and,
Z represents the atoms necessary to complete a 5- to 6-membered heterocyclic nucleus *including the substituted nitrogen atom, carbon atoms and up to one or more other heteroatoms chosen from the group consisting of nitrogen, oxygen, sulfur and selenium atoms.*

11. The image-forming element as defined in claim 10 wherein Z represents the atoms necessary to complete a member selected from the group consisting of a pyridine nucleus, *and* a quinoline nucleus [and an indole nucleus].

[12. The image-forming element as defined in claim 10 wherein $R_1$ is a methine linkage terminated by a 5- to 6-membered heterocyclic nucleus.]

13. The process which comprises imagewise exposing to visible light the image-forming element defined in claim 10 and forming a visible image in the energy-sensitive composition layer.

14. The process which comprises subjecting the image-forming element defined in claim 10 to an imagewise pattern of electromagnetic radiation and forming a visible image in the energy-sensitive composition layer.

15. An image-forming element comprising a support and at least one layer of an energy-sensitive composition comprising [a compound] *a film-forming binder and a photobleachable dye* having a formula selected from the group consisting of:

(A)

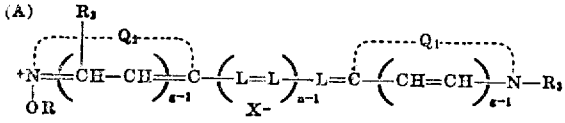

(B)

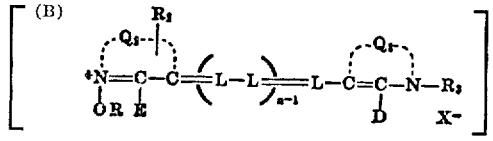

[(C)] (*B*)

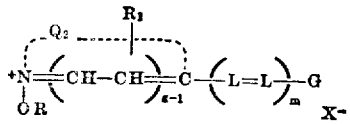

(D)

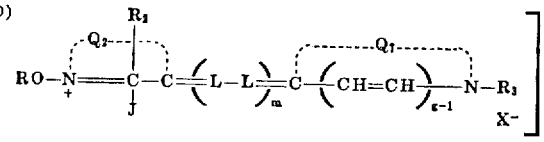

(E)

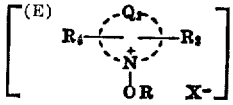

(F)

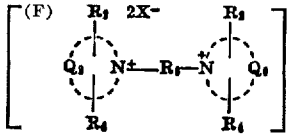

[(G)] (*C*)

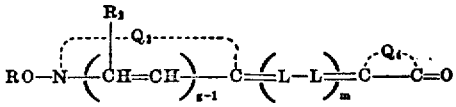

and

[(H)] (*D*)

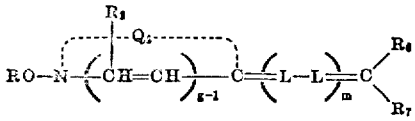

wherein:

$Q_1$, $Q_2$, [$Q_3$, $Q_4$,] *and* $Q_7$ [and $Q_9$] each represent the nonmetallic atoms necessary to complete a 5- to 6-membered heterocyclic nucleus;
*$Q_4$ represents the nonmetallic atoms necessary to complete a 5- or 6-membered heterocyclic nucleus containing car-*

*bon atoms and a heteroatom chosen from the class consisting of oxygen, sulfur, nitrogen and selenium atoms;* n is a positive integer from 1 to 4;

m is a positive integer from 1 to 3;

[$R_5$ is an alkyleneoxy radical having 1 to 8 carbon atoms in the alkylene chain;]

g is a positive integer from 1 to 2;

X is an acid anion;

L is a methine linkage;

[R is selected from the group consisting of an alkyl radical and an acyl radical;

D, E, J,] $R_2$ [and $R_4$] are each] *is* selected from the group consisting of an aryl radical, a hydrogen atom and an alkyl radical;

$R_3$ is selected from the group consisting of an alkyl radical, an alkenyl radical, an aryl radical and an alkoxy radical;

G is selected from the group consisting of an aniliovinyl radical and an aryl radical; and $R_6$ and $R_7$ are each a cyano radical.

16. The image-forming element as defined in claim 15 wherein said composition comprises [a compound] *a photobleachable dye* having the formula:

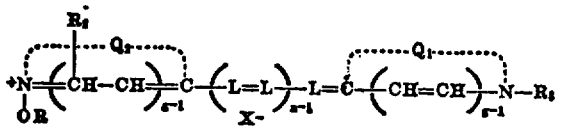

wherein R, $R_2$, $R_3$, $Q_1$, $Q_2$, L, X, g and n are as previously defined.

[17. The image-forming element as defined in claim 15 wherein said composition comprises a compound having the formula:

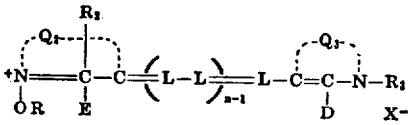

wherein R, $R_2$ $R_3$, $Q_2$, $Q_3$, L, D, E, X and n are as previously defined.]

18. The image-forming element as defined in claim 15 wherein said composition comprises [a compound] *a photobleachable dye* having the formula:

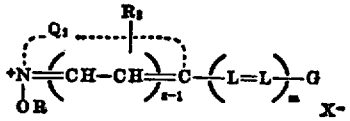

wherein R, $R_2$, $Q_2$, L, G, X, m and g are as previously defined.

[19. The image-forming element as defined in claim 15 wherein said composition comprises a compound having the formula:

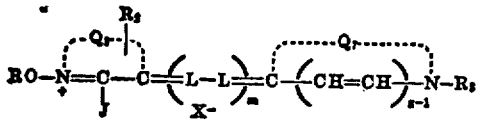

wherein R, $R_2$, $R_3$, J, $Q_2$, $Q_7$, L, X, m and g are as previously defined.]

20. The image-forming element as defined in claim 15 wherein said composition comprises [a compound] *a photobleachable dye* having the formula:

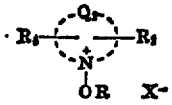

wherein R, $R_2$, $R_4$, $Q_2$ and X are as previously defined.

[21. The image-forming element as defined in claim 15 wherein said composition comprises a compound having the formula:

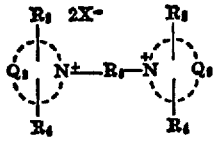

wherein $R_2$, $R_4$, $Q_2$, $Q_9$, X and $R_5$ are as previously defined.]

22. The image-forming element as defined in claim 15 wherein said composition comprises [a compound] *a photobleachable dye* having the formula:

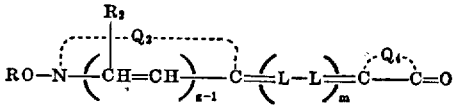

wherein: R, $R_2$, $Q_2$, $Q_4$, L, g, and m are previously defined.

23. The image-forming element as defined in claim 15 wherein said composition comprises [a compound] *a photobleachable dye* having the formula:

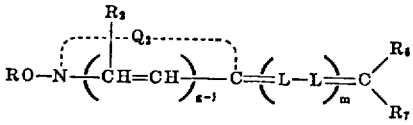

wherein: R, $R_2$, $Q_2$, g, m, $R_6$ $R_7$ and L are as previously defined.

24. A light-sensitive element comprising a support containing *a film-forming binder and* a photobleachable dye having a formula selected from the group consisting of

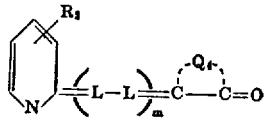

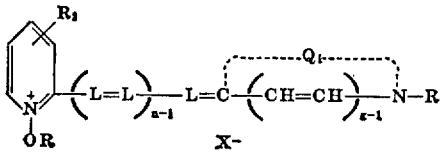

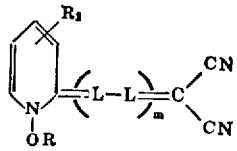

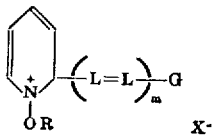

wherein:

R is selected from the group consisting of an alkyl radical and an acyl radical;

L is a methine linkage;

G is selected from the group consisting of an anilino-vinyl radical and a phenyl radical;

*m* is a positive integer from 1 to 3;

X is an acid anion;

$Q_1$ [and $Q_4$ each represent] *represents* the atoms necessary to complete a 5- to 6-member heterocyclic nucleus *including the substituted nitrogen atom, carbon atoms and up to one or more other heteroatoms chosen from the group consisting of nitrogen, oxygen, sulfur and selenium atoms;*

*$Q_4$ represents the nonmetallic atoms necessary to complete a 5- or 6-membered heterocyclic nucleus containing carbon atoms and a heteroatom chosen from the class con-*

*sisting of oxygen, sulfur, nitrogen and selenium atoms;*

$R_2$ is selected from the group consisting of an aryl radical, a hydrogen atom and alkyl radical;

n is a positive integer from 1 to 4;

$R_3$ is selected from the group consisting of an alkyl radical, an alkenyl radical, an aryl radical and alkoxy radical;

*g* is positive integer from 1 to 2.

25. The light-sensitive element of claim 24 wherein the photobleachable dye is imbibed into the support.

26. The light-sensitive element of claim 24 wherein the photobleachable dye is coated on the support.

27. The light-sensitive element of claim 24 wherein the dye is dispersed in a vehicle which is coated on the support.

28. A light-sensitive element comprising a support having coated thereon a composition comprising gelatin and 3′ - ethyl-1-methoxy-4′,5′-benzo-2-pyridothiacarbocyanine perchlorate.

29. A photographic element for producing positive color images from color originals comprising a support having coated thereon an energy-sensitive composition comprising:

a. a cyan dye,
b. a magenta dye,
c. a yellow dye, and
d. a polymeric film-forming binder, said dyes having the formula:

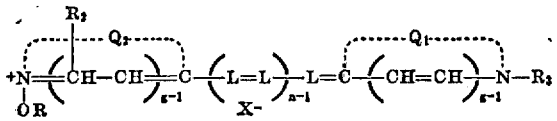

wherein:

$Q_2$ represents the atoms necessary to complete a 5- to 6-membered heterocyclic nucleus *including the substituted nitrogen atom, carbon atoms and up to one or more other heteroatoms chosen from the group consisting of nitrogen, oxygen, sulfur and selenium atoms;*

R is selected from the group consisting of:
  a. an alkyl radical and
  b′ an acyl radical;

$R_2$ is selected from the group consisting of:
  a. an aryl radical,
  b. a hydrogen atom, and
  c. an alkyl radical;

L is a methine linkage;

X is an acid anion;

g is a positive integer from 1 to 2;

n is a positive integer from 1 to 4;

$Q_1$ represents the nonmetallic atoms required to complete a heterocyclic nucleus containing from 5 to 6 atoms in the heterocyclic ring *including the substituted nitrogen atom carbon atoms and up to one or more other heteroatoms chosen from the group consisting of nitrogen, oxygen, sulfur and selenium atoms;* and $R_3$ is selected from the group consisting of an alkyl radical, an alkenyl radical, an aryl radical and an alkoxy radical.

30. A light-sensitive element for producing positive color images from color originals comprising a support having coated thereon a composition comprising a. 3′-ethyl-1-methoxy - 4′,5′ - benzo - 2 - pyridothiacarbocyanine perchlorate;
b. 3′-ethyl - 1 - methoxy - 2 - pyridothiadicarbocyanine perchlorate;
c. 1-ethoxy - 3′ - ethyl - 2 - pyridothiacyanine tetrafluoroborate and
d. a polymeric film-forming binder.

31. A process for forming an image which comprises exposing an energy-sensitive element in an imagewise manner to electromagnetic energy, said element comprising a support having coated thereon a layer of a composition comprising [a compound] *a film-forming binder and a photobleachable dye* having a formula selected from the group consisting of:

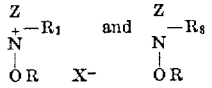

wherein:

$R_1$ is selected form the group consisting of a methine linkage terminated by a *5- or 6-membered* heterocyclic nucleus of the type contained in cyanine dyes *containing carbon atoms and at least one heteroatom chosen from the class consisting of oxygen, sulfur, nitrogen, and selenium atoms* [an alkyl radical,] an anilino vinyl radical, [a hydrogen atom,] an aryl radical, [an aldehyde group,] *and* a styryl radical;

$R_8$ is selected from the group consisting of:
  a. methine linkage terminated by a *5- or 6-membered* heterocyclic nucleus of the type contained in merocyanine dyes *containing carbon atoms and at least one heteroatom chosen from the class consisting of oxygen, sulfur, nitrogen, and selenium atoms* and
  b. an allylidene radical;

R is selected from the group consisting of an alkyl radical and an acyl radical;

X is an acid anion, and

Z represents the atoms necessary to complete a 5- to 6-membered heterocyclic nucleus *including the substituted nitrogen atom, carbon atoms and up to one or more other heteroatoms chosen from the group consisting of nitrogen, oxygen, sulfur and selenium atoms.*

32. The process of claim 31 wherein Z represents the atoms necessary to complete a member selected from the group consisting of a pyridine nucleus, *and* a quinoline nucleus [and an indole nucleus].

[33. The process of claim 31 wherein $R_1$ is a methine linkage terminated by a 5- to 6-membered heterocyclic nucleus.]

34. A process for forming an image which comprises exposing an energy-sensitive element in an imagewise manner to electromagnetic energy, said element comprising a support having coated thereon a layer of a composition comprising [a compound] *a film-forming binder and a photobleachable dye* having a formula selected from the group consisting of:

(A)

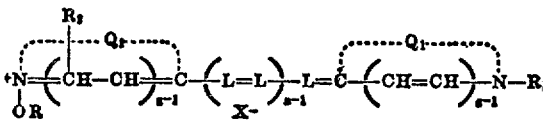

(B)

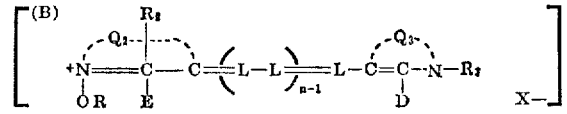

[(C)] (*B*)

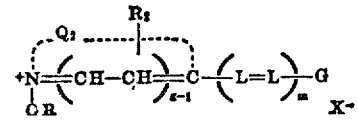

(D)

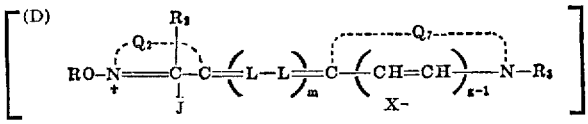

[(E)] (*C*)

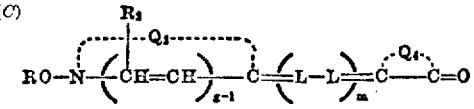

[(F)] (D)

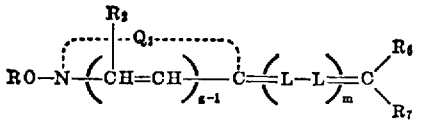

and

[(G)] (E)

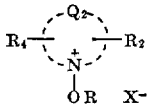

[and (H)

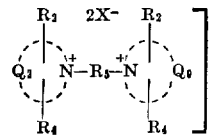

]

wherein:

$Q_1$, $Q_2$, [$Q_3$, $Q_4$], *and* $Q_7$ [and $Q_9$] each represent the nonmetallic atoms necessary to complete a 5-to-6-membered heterocyclic nucleus *including the substituted nitrogen atom, carbon atoms and up to one or more other heteroatoms chosen from the group consisting of nitrogen, oxygen, sulfur and selenium atoms;*

*$Q_4$ represents the nonmetallic atoms necessary to complete a 5- or 6-membered heterocyclic nucleus containing carbon atoms and a heteroatom chosen from the class consisting of oxygen, sulfur, nitrogen and selenium atoms;* n is a positive integer from 1 to 4;

m is a positive integer from 1 to 3;

g is a positive integer from 1 to 2;

X is an acid anion;

L is a methine linkage;

[$R_5$ is an alkyleneoxy radical having 1 to 8 carbon atoms in the alkylene chain;]

R is [selected from the group consisting of an alkyl radical and] an acyl radical;

[D, E, J,]$R_2$ and $R_4$ are each selected from the group consisting of an aryl radical, hydrogen atom and an alkyl radical;

$R_6$ and $R_7$ are each cyano radicals;

$R_3$ is selected from the group consisting of an alkyl radical an alkenyl radical, an aryl radical and an alkoxy radical; and G is selected from the group consisting of an anilinovinyl radical and an aryl radical.

35. The process of claim 34 wherein said [compound] *photobleachable dye* has the formula:

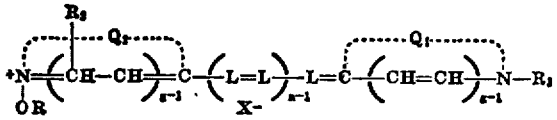

wherein R, $R_2$, $R_3$, $Q_1$, $Q_2$, L, X, g and n are as previously defined.

[36. The process of claim 34 wherein said compound has the formula:

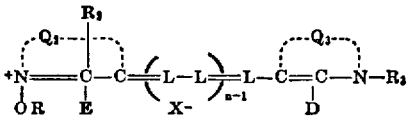

wherein R, $R_2$, $R_3$, $Q_2$, $Q_3$, L, D, E, X and n are as previously defined.]

37. The process of claim 34 wherein said [compound] *photobleachable dye* has the formula:

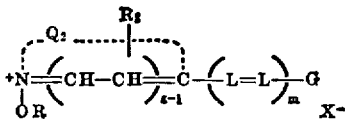

wherein R, $R_2$, $Q_2$, L, G, X, m and g are as previously defined.

[38. The process of claim 34 wherein said compound has the formula:

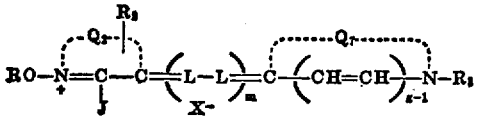

wherein R, $R_2$, $R_3$, J, $Q_2$, $Q_7$, L, X, *m* and *g* are as previously defined.]

39. The process of claim 34 wherein said [compound] *photobleachable dye* has the formula:

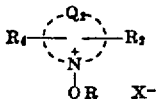

wherein R, $R_2$, $R_4$, $Q_2$ and X are as previously defined.

[40. The process of claim 34 wherein said compound has the formula

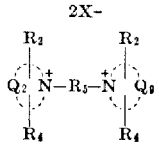

wherein $R_2$, $R_4$, $Q_2$, $Q_9$, X and $R_5$ are as previously defined.]

41. The process of claim 34 wherein said [compound] *photobleachable dye* has the formula:

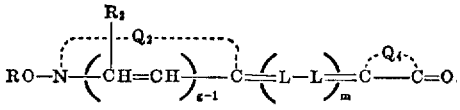

wherein:

R, $R_2$, L, $Q_2$, $Q_4$ g and m are as previously defined.

42. The process of claim 34 wherein said [compound] *photobleachable dye* has the formula:

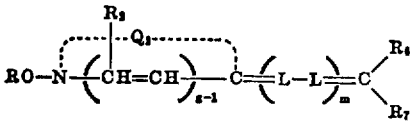

wherein:

R, $R_2$, $Q_2$, g, m, L, $R_6$ and $R_7$ are as previously defined.

43. An image-forming composition comprising [an energy-sensitive compound] *a film-forming binder and a photobleachable dye* having the formula:

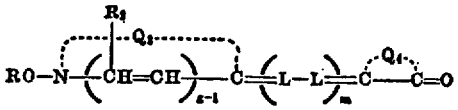

wherein:

$Q_2$ [and $Q_4$ each represent] *represents* the nonmetallic atoms necessary to complete a 5- to 6-membered heterocyclic nucleus *including the substituted nitrogen atom, carbon atoms and up to one or more other heteroatoms chosen from the group consisting of nitrogen, oxygen, sulfur and selenium atoms;*

*$Q_4$ represents the nonmetallic atoms necessary to complete a 5- or 6-membered heterocyclic nucleus containing carbon atoms and a heteroatom chosen from the class consisting of oxygen, sulfur, nitrogen and selenium atoms;*

R is selected from the group consisting of:

a. an alkyl radical and b. an acyl radical;

$R_2$ is selected from the group consisting of:

a. an aryl radical, b. a hydrogen atom and c. an alkyl radical;

L is a methine linkage;

g is a positive integer from 1 to 2; and m is a positive integer from 1 to 3.

44. The image-forming composition of claim 43 wherein $Q_2$ represents the atoms necessary to complete a member selected from the group consisting of a pyridine nucleus, *and* a quinoline nucleus [and an indole nucleus].

45. An image-forming composition comprising [an energy-sensitive compound] *a film-forming binder and a photobleachable dye* having the formula:

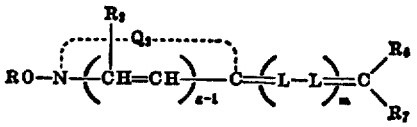

wherein:

$Q_2$ represents the nonmetallic atoms necessary to complete a 5- to 6-membered heterocyclic nucleus *including the substituted nitrogen atom, carbon atoms and up to one or more other heteroatoms chosen from the group consisting of nitrogen, oxygen, sulfur and selenium atoms;*

R is selected from the group consisting of:

a. an alkyl radical and b. an acyl radical;

$R_2$ is selected from the group consisting of:

a. an aryl radical, b. a hydrogen atom and c. an alkyl radical;

L is a methine linkage;

g is a positive integer from 1 to 2;

m is a positive integer from 1 to 3; and $R_7$ [$R_5$] and $R_6$ are each a cyano radical.

46. The image-forming composition of claim 45 wherein $Q_2$ represents the atoms necessary to complete a member selected from the group consisting of a pyridine nucleus, *and* a quinoline nucleus [and an indole nucleus].

References Cited

The following references, cited by the Examiner, are of record in the patented file of this patent or the original patent.

UNITED STATES PATENTS

| | | | |
|---|---|---|---|
| 3,532,499 | 10/1970 | Willems et al. | 96—95 |
| 3,582,342 | 6/1971 | Itano et al. | 96—90 R |
| 3,615,432 | 10/1971 | Jenkins et al. | 96—88 |
| 2,991,285 | 7/1961 | Feely | 260—287 |

OTHER REFERENCES

Bauer et al., "The Substitution of Quinoline 1-oxide by Mercaptans" J. Org. Chem. 31 (3), 939–41 (1966) Chem. Abs. 64:12638.

Titkova et al. "Some Reactions of 1-alkoxypyridinium Salts" Zh Obsch Khim 34(12), 4126 (1964) Chem. Abs. 62:9098.

Brink, "Prep. of Styrylpyridines from N-alkoxy-pyridinium Salts" Tydskr. Natuurwetenskappe 3, 70–80 (1963) Chem. Abs. 60.

J. TRAVIS BROWN, Primary Examiner

U.S. Cl. X.R.

96—20, 67, 73, 89